US009585649B2

(12) United States Patent
Blain et al.

(10) Patent No.: US 9,585,649 B2
(45) Date of Patent: Mar. 7, 2017

(54) RETRACTOR

(71) Applicant: SPINAL ELEMENTS, INC., Carlsbad, CA (US)

(72) Inventors: Jason Blain, Encinitas, CA (US); Eric Kovach, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 82 days.

(21) Appl. No.: 14/263,927

(22) Filed: Apr. 28, 2014

(65) Prior Publication Data

US 2014/0257044 A1 Sep. 11, 2014

Related U.S. Application Data

(60) Continuation of application No. 13/786,200, filed on Mar. 5, 2013, now Pat. No. 8,740,786, which is a (Continued)

(51) Int. Cl.
*A61B 17/02* (2006.01)
*A61B 1/32* (2006.01)
(Continued)

(52) U.S. Cl.
CPC .............. *A61B 17/025* (2013.01); *A61B 1/32* (2013.01); *A61B 17/0206* (2013.01); (Continued)

(58) Field of Classification Search
CPC ............................................ A61B 2017/0256
See application file for complete search history.

(56) References Cited

U.S. PATENT DOCUMENTS 569,839 A 10/1896 Roeloffs
1,613,141 A * 1/1927 Stein .............................. 600/232
(Continued)

FOREIGN PATENT DOCUMENTS

WO WO 2016/040497 3/2016

*Primary Examiner* — Jan Christopher Merene
(74) *Attorney, Agent, or Firm* — Knobbe, Martens, Olson & Bear, LLP

(57) ABSTRACT

A retractor for use in surgical operations comprises a pair of blade assemblies which are adapted to open about a set of axes that are not parallel to a third spatial axis. The retractor further comprises a pair of arms, which are adapted to move the pair of blade assemblies apart from one another in the third spatial axis. In operation, the blade assemblies are closed to assume a low profile, inserted into a relatively small incision, and stretched apart from each other, thereby stretching the skin about the incision to form an aperture longer than the incision. The blade assemblies are then opened by rotating the blades about the set of axes, thereby stretching the skin around the incision in a second direction that is substantially perpendicular to the first direction (i.e. the direction of the incision.) The retractor thus forms an aperture for passage of surgical instruments and viewing of the surgical field by surgical personnel. In some embodiments, the retractor features a pair of removable handles that may be removed from the arms during surgery in order to afford the surgeon improved space management about the incision. In specific embodiments, the invention provides a method of performing an operation, e.g. a spinal operation, on a patient using the disclosed retractor.

16 Claims, 22 Drawing Sheets

Related U.S. Application Data continuation of application No. 13/352,676, filed on Jan. 18, 2012, now Pat. No. 8,409,091, which is a division of application No. 11/861,149, filed on Sep. 25, 2007, now Pat. No. 8,142,355.

(60) Provisional application No. 60/826,888, filed on Sep. 25, 2006.

(51) Int. Cl.
*A61B 17/28* (2006.01)
*A61B 17/00* (2006.01)

(52) U.S. Cl.
CPC ........... *A61B 2017/00367* (2013.01); *A61B 2017/0256* (2013.01); *A61B 2017/2837* (2013.01)

(56) References Cited

U.S. PATENT DOCUMENTS

| | | | |
|---|---|---|---|
| 1,822,280 A | 9/1931 | Ervay | |
| 2,002,021 A * | 5/1935 | Rouse | 606/105 |
| 2,670,731 A * | 3/1954 | Zoll et al. | 600/232 |
| 4,156,424 A * | 5/1979 | Burgin | 600/213 |
| 5,113,846 A | 5/1992 | Hiltebrandt et al. | |
| 5,363,841 A | 11/1994 | Coker | |
| 5,618,260 A | 4/1997 | Caspar et al. | |
| 5,681,265 A * | 10/1997 | Maeda et al. | 600/219 |
| 5,931,777 A | 8/1999 | Sava | |
| 5,931,778 A * | 8/1999 | Furnish | 600/232 |
| 5,980,455 A | 11/1999 | Daniel et al. | |
| 6,042,540 A * | 3/2000 | Johnston et al. | 600/213 |
| 6,264,650 B1 | 7/2001 | Hovda et al. | |
| 7,087,055 B2 | 8/2006 | Lim et al. | |
| 7,229,408 B2 | 6/2007 | Douglas et al. | |
| 7,390,298 B2 | 6/2008 | Chu | |
| 7,481,766 B2 * | 1/2009 | Lee et al. | 600/214 |
| 7,491,168 B2 | 2/2009 | Raymond et al. | |
| 7,582,058 B1 | 9/2009 | Miles et al. | |
| 7,594,888 B2 | 9/2009 | Raymond et al. | |
| 7,722,613 B2 | 5/2010 | Sutterlin et al. | |
| 7,846,183 B2 | 12/2010 | Blain | |
| 8,062,217 B2 | 11/2011 | Boucher et al. | |
| 8,142,355 B2 | 3/2012 | Blain et al. | |
| 8,409,091 B2 | 4/2013 | Blain et al. | |
| 8,740,786 B2 | 6/2014 | Blain et al. | |
| 2002/0123668 A1 | 9/2002 | Ritland | |
| 2005/0102029 A1 | 5/2005 | Blain | |
| 2005/0107877 A1 | 5/2005 | Blain | |
| 2005/0159651 A1 | 7/2005 | Raymond et al. | |
| 2005/0159818 A1 | 7/2005 | Blain | |
| 2005/0192574 A1 | 9/2005 | Blain | |
| 2006/0004261 A1 | 1/2006 | Douglas | |
| 2006/0074278 A1 | 4/2006 | Petit et al. | |
| 2006/0074425 A1 | 4/2006 | Sutterlin et al. | |
| 2006/0106416 A1 | 5/2006 | Raymond et al. | |
| 2006/0224044 A1 | 10/2006 | Marchek et al. | |
| 2006/0235423 A1 | 10/2006 | Cantu | |
| 2007/0073111 A1 * | 3/2007 | Bass | 600/215 |
| 2008/0114208 A1 | 5/2008 | Hutton et al. | |
| 2008/0132766 A1 | 6/2008 | Dant et al. | |
| 2010/0114110 A1 | 5/2010 | Taft et al. | |
| 2011/0034777 A1 | 2/2011 | Ames et al. | |
| 2012/0245431 A1 | 9/2012 | Baudouin et al. | |
| 2013/0190575 A1 | 7/2013 | Mast et al. | |
| 2013/0204090 A1 | 8/2013 | Blain et al. | |
| 2014/0148652 A1 | 5/2014 | Weiman | |
| 2014/0257035 A1 | 9/2014 | Blain | |

* cited by examiner

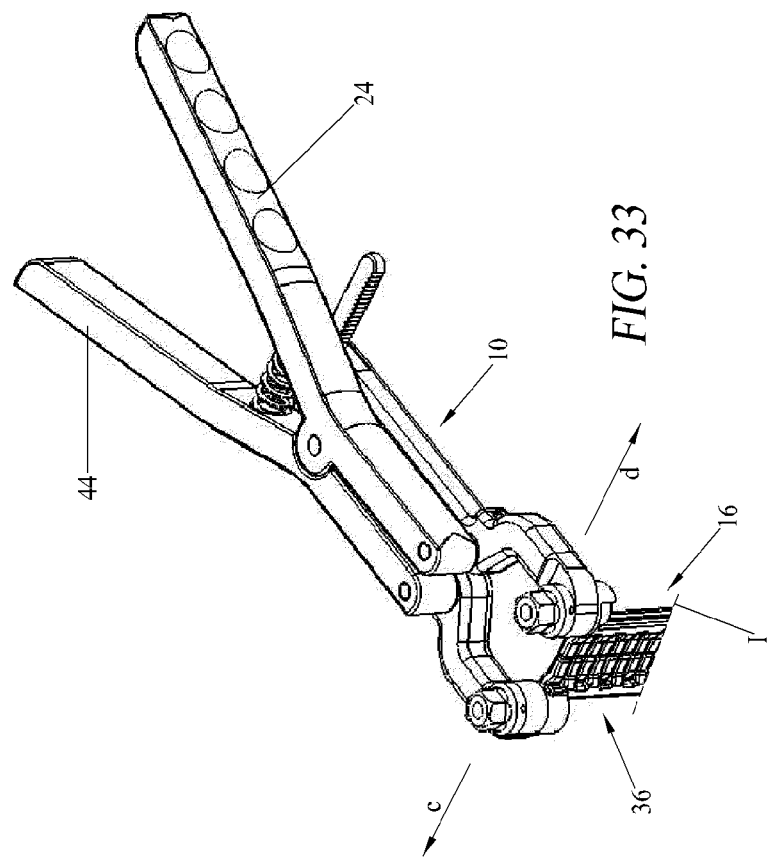
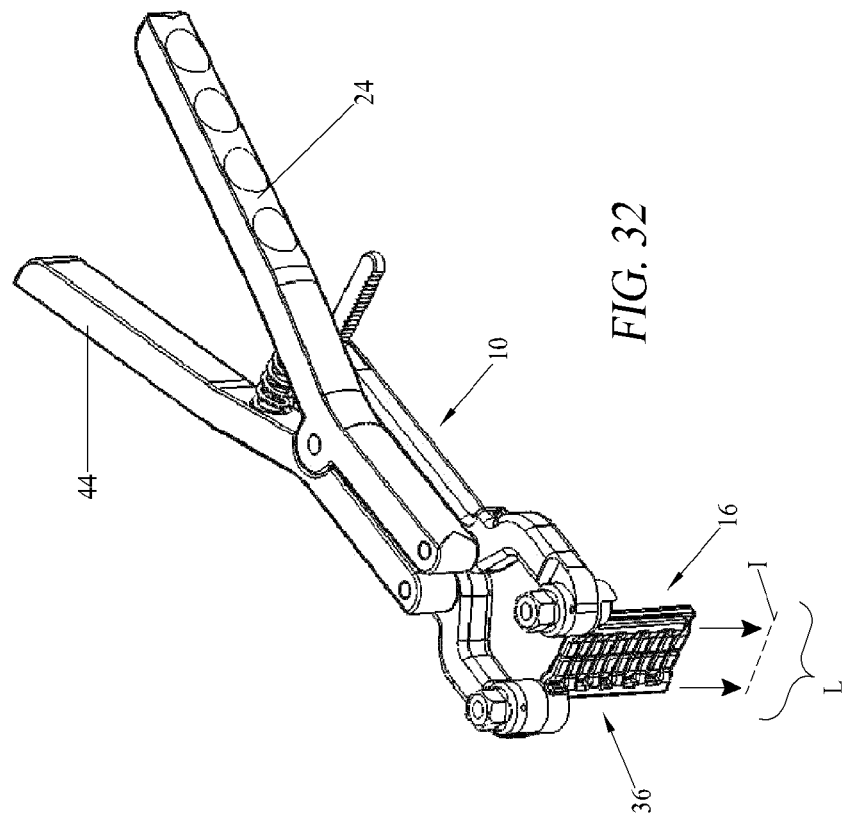

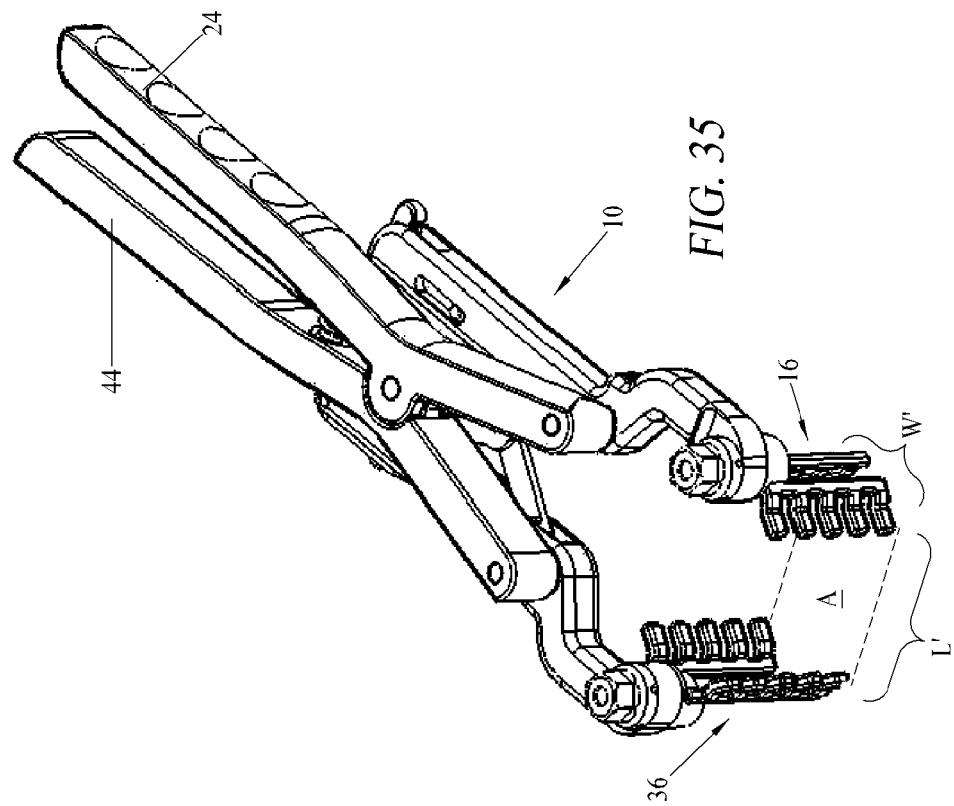
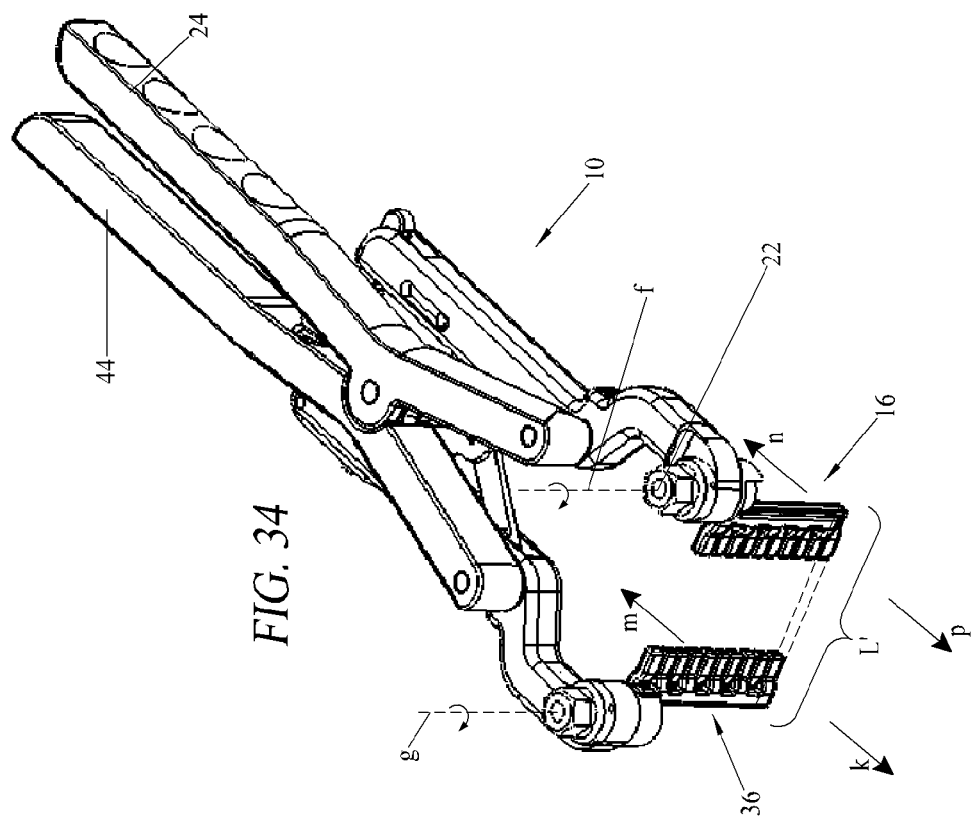

RETRACTOR

CROSS-REFERENCE TO RELATED APPLICATIONS

Any and all applications for which a foreign or domestic priority claim is identified in the Application Data Sheet as filed with the present application, are hereby incorporated by reference in their entirety under 37 CFR 1.57.

FIELD OF THE INVENTION

The present invention relates to the field of surgery and more particularly to a retractor for use in inter alia surgery of the lower back.

BACKGROUND OF THE INVENTION

Retractors are surgical devices used to spread bodily tissues in order to allow a surgeon or surgical assistant to see and access a part of the body that is to be surgically treated. In general, retractors comprise a pair of jaws or blades that grip the bodily tissue and push it apart under the force generated by an actuator, such as a pair of scissor-like arms having a distal end and a proximal end. The proximal end generally defines a pair of handles and the distal end attaches to the pair of blades so that manipulation of the handles causes the blades to move apart from one another. Once an incision is made in the body to be operated on, the blades are inserted into the incision and the actuator is manipulated to move the blades of the retractor apart, thus spreading the tissue and providing an aperture through which the surgeon can access visualize the tissue to be surgically treated. One problem with this type of retractor is that the aperture size is generally limited by the size of the incision, meaning that a large aperture requires a relatively large incision. The drawback to this arrangement is that larger incisions result in the need for longer periods for healing of the incision. There is thus a need for a surgical retractor that is capable of creating a relatively large aperture using a relatively small incision, thereby reducing the invasiveness of the surgical procedure, post-operative healing times and patient discomfort.

SUMMARY OF THE INVENTION

The foregoing and other needs are met by embodiments of the present invention, which provide a retractor (surgical retractor) comprising: (a) a first blade assembly comprising a first blade rotatable about a first axis, a second blade rotatable about said first axis and an adjuster in mechanical communication with the first and second blades and adapted to rotate the first and second blades relative to each other about said first axis; (b) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (c) a means for moving said first blade assembly relative to said second blade assembly along a third axis that is not parallel to said first and second axes.

Further needs are met by embodiments of the present invention, which provide a method comprising the steps of: (a) providing a retractor comprising: (i) a first blade assembly comprising a first blade rotatable about a first axis, a second blade rotatable about said first axis and an adjuster in mechanical communication with the first and second blades and adapted to rotate the first and second blades relative to each other about said first axis; (ii) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (ii) a means for moving said first blade assembly relative to said second blade assembly along a third axis that is not parallel to said first and second axes; (b) adjusting the first and second blades of the first blade assembly to be substantially parallel to each other to form a first closed blade assembly; (c) adjusting the third blade, and when present the fourth blade, of the second blade assembly to be substantially parallel to the first and second blades of the first blade assembly; (d) making an incision in a tissue of a body; (e) inserting said first blade assembly and said second blade assembly within the incision; (f) moving the first blade assembly away from the second blade assembly along said third axis and along the length of the incision so that the incision is stretched to create an opening longer than the incision; and (g) adjusting the first and second blades of the first blade assembly about said first axis to an open position, and, when said fourth blade of said second blade assembly is present, adjusting the third and fourth blades of the second blade assembly substantially about said second axis to an open position, thereby stretching the incision out from said third axis and creating an aperture in the tissue that is longer and wider than the incision.

Other needs are met by embodiments of the invention, which provide a retractor comprising: (a) a first arm having a distal end and a proximal end; (b) a second arm having a distal end and a proximal end; (c) a first blade assembly, attached near the distal end of the first arm and comprising a first blade, a second blade and an adjuster in mechanical communication with the first and second blades and adapted to rotate the first and second blades relative to each other about a first axis; (d) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (e) an actuator adapted to move at least the distal ends of said first and second arms relative to each other along a third axis that is not parallel to the first and second axes.

Further needs are met by embodiments of the present invention, which provide a method comprising the steps of: (a) providing a retractor comprising: (i) a first arm having a distal end and a proximal end; (ii) a second arm having a distal end and a proximal end; (iii) a first blade assembly, attached near the distal end of the first arm and comprising a first blade, a second blade and an adjuster in mechanical communication with the first and second blades and adapted to rotate the first and second blades relative to each other about a first axis; (iv) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (v) an actuator adapted to move at least the distal ends of said first and second arms relative to each other along a third axis that is not parallel to the first and second axes; (b) ensuring that the first and second blades of the first blade assembly are substantially parallel to each other to form a first closed blade assembly; (c) ensuring that the third blade, and when present the fourth blade, of the second blade assembly are substantially parallel to the first and second blades of the first blade assembly; (d) making an incision in a tissue of a body; (e) inserting said first blade assembly and said second blade assembly within the incision; (f) actuating the retractor such that said first blade assembly and second blade assembly are moved apart from one another along the second axis and the incision is stretched along the length of the incision to create an opening longer than the incision; and (g) adjusting the first and second blades of the first blade assembly along said first axis to an open position, and, when said fourth blade of said second blade assembly is present, adjusting the third and fourth blades of the second blade assembly substantially along said second axis to an open position, thereby stretching the incision along the first axis and creating an aperture in the tissue that is longer and wider than the incision.

Further needs are met by embodiments of the present invention, which provide a retractor comprising: (a) a first arm having a distal end and a proximal end; (b) a second arm having a distal end and a proximal end, at least said distal end of said second arm and said distal end of said second arm being movable toward and away from each other; (c) a first blade assembly attached near the distal end of the first arm, which comprises a first blade, a second blade and a means for moving said first and second blades relative to each other about a first axis to adopt at least an opened position and a closed position; (d) a second blade assembly attached near the distal end of the second arm, which comprises a third blade, a fourth blade and a means for moving said third and fourth blades relative to each other about a second axis different from said first axis; and (e) a means for moving at least said distal end of said first arm and said distal end of said second arm relative to one another along a third axis that is not parallel to said first and second axes.

Additional needs are met by embodiments of the present invention, which provide a method comprising the steps of: (a) providing a retractor comprising: (i) a first arm having a distal end and a proximal end; (ii) a second arm having a distal end and a proximal end, at least said distal end of said second arm and said distal end of said second arm being movable toward and away from each other; (iii) a first blade assembly attached near the distal end of the first arm, which comprises a first blade, a second blade and a means for moving said first and second blades relative to each other along a first axis to adopt at least an opened position and a closed position; (iv) a second blade assembly attached near the distal end of the second arm, which comprises a third blade, a fourth blade and a means for moving said third and fourth blades relative to each other substantially along the first axis to adopt at least an opened position and a closed position; and (v) a means for moving at least said distal end of said first arm and said distal end of said second arm relative to one another along a second axis; (b) ensuring that the first and second blades of the first blade assembly are substantially parallel to each other; (c) ensuring that the third and fourth blades of the second blade assembly are substantially parallel to each other and to the first and second blades of the first blade assembly; (d) making an incision in a tissue of a body; (e) inserting said first blade assembly and said second blade assembly within the incision; (f) actuating the retractor such that said first blade assembly and second blade assembly are moved apart from one another along the second axis and the incision is stretched along the length of the incision to create an opening longer than the incision; and (g) adjusting the first and second blades of the first blade assembly along said first axis to an open position, and, when said fourth blade of said second blade assembly is present, adjusting the third and fourth blades of the second blade assembly substantially along said second axis to an open position, thereby stretching the incision along the first axis and creating an aperture in the tissue that is longer and wider than the incision.

The foregoing and additional needs are met by embodiments of the invention described herein, which provide a retractor blade assembly, comprising: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope, (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (e) a rod fitting through the passage such that movement of the plunger along the axis causes the first barrel to rotate in a first direction and the second barrel to rotate in a second direction opposite the first direction; (f) a holder possessing a third lumen, wherein the second barrel fits within the third lumen; and (g) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions.

In some embodiments, both blade assemblies open so that when placed within the incision, both blades stretch the skin in a direction substantially perpendicular or oblique to the third axis. In some embodiments, the retractor has a lock, e.g. a ratchet lock, adapted to hold the retractor in an open position (i.e. the two arms spread apart from one another). In some embodiments, at least one blade is comb-shaped, having two or more teeth adapted to engage the skin and pull it apart. In some such embodiments, the comb-shaped teeth are interweaving so that they interlock when the blade assemblies are closed. In other embodiments, at least one blade is fan shaped in that it does not possess teeth. Such fan shaped blades may be substantially flat or may be bent or beveled in order to enhance the ability of the blades to lie flat when the blade assemblies are closed. In general, each blade assembly is hinged about an axis so that the blades open and close like the covers on a book. This arrangement causes the blade assembly to exert force on the skin about an incision in opposing directions substantially perpendicular to the blade assembly axes and perpendicular or oblique to a cord defined by the points at which the blade assembly axes intersect the arms of the retractor. In some embodiments, the retractor includes a stabilizer, which maintains both arms parallel to one another. In particular embodiments, such a stabilizer comprises a set of cross members between two substantially parallel arms, which move in such a way that as the arms open and close (i.e. move away from and toward one another, respectively), they are held in an attitude that is substantially parallel to one another. In some such embodiments, the actuator comprises a first handle connected to the proximal end of the first arm and a second handle connected to the proximal end of the second handle. This pair of handles may be removable. Additionally, the pair of handles may include a biasing member (e.g. a biasing spring) to hold the two handles apart. In some other embodiments, the arms are scissor-like arms, which cross one another and pivot about a pivot point. In such cases, although reference is made to a third axis, which passes through the blade assemblies at an angle perpendicular or oblique to the blade assemblies, it is to be understood that the actual opening and closing of a scissor-like pair of arms causes the ends of the arms to move in an arc. In some such embodiments, each handle forms, along with its corresponding arm, and integral unit. In other embodiments, the handles may be removable. Indeed, the blade assemblies, which fit at the ends of the arms, may be removable as well. In some embodiments, the retractor may be provided to a surgeon or surgical personnel in the form of a kit comprising additional surgical articles and optionally instructions for the use and handling of the retractor. Such additional surgical articles may include: scalpels, suture needles, pedicle screws, suture material, spinal implant material, spinal fusion rods, biocompatible adhesive and closure staples.

In some embodiments, the methods of the invention are surgical methods that include making an incision through a patient's skin. The methods of using the present invention are especially well suited for performing less invasive surgery, especially in the spinal region, and most especially in the lumbar region of the spine. In some embodiments, the incision is made in the lumbar region of the back near the spine; and in some particular embodiments, the method includes placing one or more pedicle screws in the spine. The pedicle screws are passed through the incision that is held open by the retractor of the invention, which permits the surgeon an excellent field of view of the area being operated on as well as ample space for passing the various surgical articles through the incision, while at the same time providing an incision which readily returns to its initial short length when the retractor is removed. Indeed one of the advantages of using the retractor of the present invention is that removal of the retractor after the operation has been finished results in the incision to substantially the same shape and size as prior to retractor insertion. Thus, the retractor of the invention supports and makes possible less invasive surgery than heretofore was permitted with known retractors.

Such a retractor permits insertion of a relatively compact set of retractor blades into a relatively short incision, opening of the incision in two non-parallel directions to make a surgical aperture that is longer than the incision, and closing of the incision to present a relatively short incision for the surgical professional to close. By stretching the tissue around the incision in two non-parallel directions, the retractor of the invention allows the surgeon to make a much smaller incision than is generally necessary using previously known retractors. Thus, the retractor of the invention permits the surgical professional to make less invasive incisions, while simultaneously permitting the professional to view and access the tissue that is to be surgically treated. Less invasive incisions generally provide shorter patient recovery times, decreased patient discomfort and overall improved outcomes as compared to the larger incisions necessitated by the prior art retractors.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 23-24 show side views of a first blade of a blade assembly, while

FIGS. 30 and 31 show the relationship between the angles of slots in the first blade and the second blade of the blade assembly.

FIGS. 32-35 show perspective views of a retractor of the invention in operation. A surgeon makes an incision having length L, into which the closed blade assemblies of the retractor are inserted. The surgeon then opens the retractor to create a lengthwise opening having length L', wherein L'>L. Finally the surgeon opens the blade assemblies to create a L'×W' aperture. In some embodiments, the handles 24, 44 can be removed from the arm assembly to permit the surgeon even greater ability to see and operate on the tissue to be treated.

DETAILED DESCRIPTION OF THE INVENTION

Figure 1:
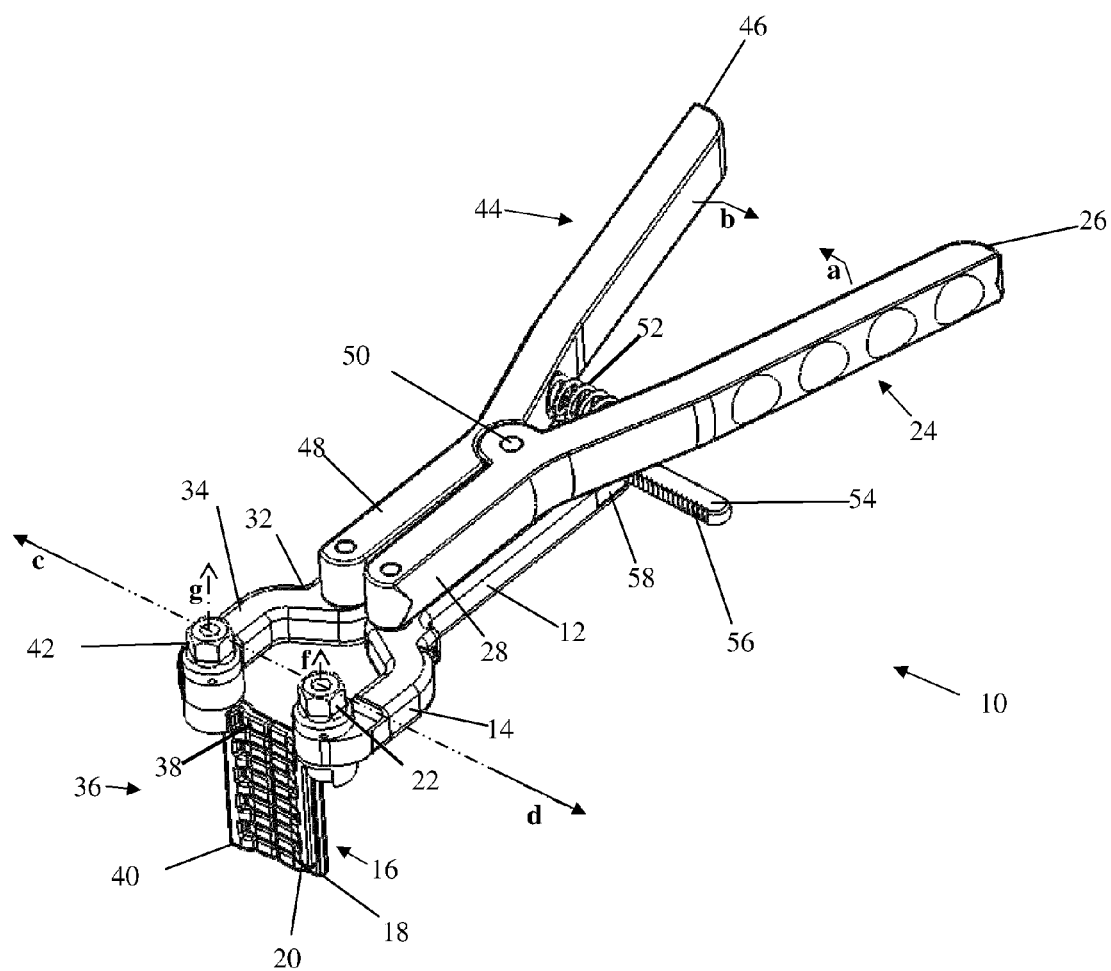
FIG. 1 provides a perspective view of a retractor of the invention with a pair of blade assemblies in a closed and parallel configuration.

The retractor of the invention provides advantages over the prior art retractors comprising a set of blades and an actuator, such as a set of scissor arms. The retractor of the invention allows the person skilled in the art to insert a relatively compact set of retractor blades into an incision having a short length. In some embodiments, the compact set of retractor blades are of such a size that they can be inserted within the incision so that they are snugly embraced by the side walls of the incision. Activation of an actuator causes the blades to move apart in a direction that is essentially parallel to the length of the incision. This causes the tissue to stretch in one direction, creating an opening having a length in that direction that is substantially longer than the incision. Once the retractor is opened in the first direction, the actuator may be locked open. Then a pair of adjusters on the blade assemblies may be manipulated to open the blade assemblies, thus pulling the incised tissue apart in directions that are not parallel to the incision. In some embodiments, these directions may be perpendicular, substantially perpendicular or oblique to the incision. Thus there is opened up an aperture that is substantially longer than the incision, and thus is substantially larger than would be possible using a prior art device. Thus in relative terms, the surgeon may use a smaller incision, and in some cases a much smaller incision, than would have been required with a prior art device. Moreover, removal of the retractor, e.g. by closing the blade assemblies, replacing the handles (if necessary), closing the arm assembly and removing the blade assemblies from the incision, causes the incision to relax back to a size that is much smaller than would have resulted from use of the prior art retractor.

In some embodiments, the handles, the blade assemblies or both are removable. In some embodiments, the blades of the blade assemblies may take on a variety of shapes and sizes. In some embodiments, the invention provides a kit comprising a plurality of retractors having blades of various sizes, shapes or both. In some currently preferred embodiments, the invention provides a kit comprising one or more sets of handles, one or more arm assemblies and two or more blade assemblies (optionally of varying blade sizes and/or shapes). In some embodiments, the invention provides a kit comprising a retractor of the invention, optionally more than two blades, at least two of which differ from one another in size, shape or both, and one or more pedicle screws for performing lumbar surgery. Thus, the invention provides a retractor of the invention, a variety of surgical kits for performing surgery, especially back surgery, and methods of using the retractor to perform surgery, and especially back surgery.

The foregoing and further needs are met by embodiments of the invention, which provide (a) a retractor comprising: (a) a first blade assembly comprising a first blade rotatable about a first axis, a second blade rotatable about said first axis and an adjuster in mechanical communication with the first and second blades and adapted to rotate the first and second blades relative to each other about said first axis; (b) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (c) a means for moving said first blade assembly relative to said second blade assembly along a third axis that is not parallel to said first and second axes. It is to be understood by one of ordinary skill in the art that, while at present a preferred embodiment of the invention uses a means for moving said first blade assembly relative to said second blade assembly employs two arms that are held parallel to one another by a means for stabilizing the arms, it is also possible for said means for moving said first blade assembly relative to said second blade assembly to be a pair of crossing arms joined to one another at a pivot point. In such cases, the blade assemblies move relative to one another along an arc. Nonetheless, their general direction of motion relative to one another, and the direction of motion that is of especial interest in the context of the present invention, is along an axis that is generally defined by a line passing through the blade assemblies, e.g. at the point where each blade assembly is attached to its respective arm. In particular embodiments, the second blade assembly comprises a third blade, a fourth blade and an adjuster in mechanical communication with the third and fourth blades and adapted to rotate the third and fourth blades relative to each other about said second axis. In some such embodiments, the first and second axes may be substantially coplanar with one another. Indeed in some currently preferred embodiments, the first and second axes are not only coplanar but also substantially parallel to one another. In particular embodiments, the first and second axes are coplanar with, parallel to, or at some pre-determined skew angle with respect to one another. In some specific examples, the third axis is substantially perpendicular to the first axis, the second axis or both the first and second axes. In particular embodiments, the third axis is substantially perpendicular to both the first axis and the second axis. In some embodiments, the third axis is perpendicular to the first axis, the second axis or both the first and second axes. In some specific embodiments, the third axis is perpendicular to both the first and second axes. In some embodiments, the retractor described herein possesses a means for locking said first and second blade assemblies in at least one predetermined position along said second axis. In some particular embodiments, two of said blades are of substantially different sizes in at least one dimension. In some specific embodiments, at least two blades of different sizes form part of the same blade assembly, while in other embodiments, two blades of different sizes form parts of different blade assemblies. In some particular embodiments, at least one of the first, second, third and, when present, forth blades is a comb-shaped blade. In some embodiments, at least one of the first, second, third and, when present, fourth blades is a substantially flat blade. In some embodiments, the invention includes at least one removable blade assembly. In some specific embodiments, both blade assemblies are removable.

In some embodiments, the invention provides a method (e.g. a method of surgery—in particular spinal surgery, e.g. in the lumbar region of the back) comprising the steps of: (a) providing a retractor comprising: (i) a first blade assembly comprising a first blade rotatable about a first axis, a second blade rotatable about said first axis and an adjuster in mechanical communication with the first and second blades and adapted to rotate the first and second blades relative to each other about said first axis; (ii) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (iii) a means for moving said first blade assembly relative to said second blade assembly along a third axis that is not parallel to said first and second axes; (b) adjusting the first and second blades of the first blade assembly to be substantially parallel to each other to form a first closed blade assembly; (c) adjusting the third blade, and when present the fourth blade, of the second blade assembly to be substantially parallel to the first and second blades of the first blade assembly; (d) making an incision in a tissue of a body; (e) inserting said first blade assembly and said second blade assembly within the incision; (f) moving the first blade assembly away from the second blade assembly along said third axis and along the length of the incision so that the incision is stretched to create an opening longer than the incision; and (g) adjusting the first and second blades of the first blade assembly about said first axis to an open position, and, when said fourth blade of said second blade assembly is present, adjusting the third and fourth blades of the second blade assembly substantially about said second axis to an open position, thereby stretching the incision out from said third axis and creating an aperture in the tissue that is longer and wider than the incision. In some such embodiments, the second blade assembly comprises a third blade, a fourth blade and an adjuster in mechanical communication with the third and fourth blades and adapted to rotate the third and fourth blades relative to each other about said second axis. In some particular embodiments, the first and second axes are substantially coplanar with one another, substantially parallel to one another and/or substantially perpendicular to the third axis. The third axis is the line passing through the points at which the blade assemblies are joined to the arms of the retractor. As mentioned above, the person skilled in the art will recognize that when the arms are scissor-like arms that cross one another and are joined at a pivot point, the motion of the blade assemblies with respect to one another will trace out an arc. However, the direction of motion of the two blade assemblies with respect to one another will be essentially along the third axis. In any case, in particular embodiments, the first and second axes are coplanar with one another, parallel to one another and/or perpendicular to the third axis. In particular embodiments, the third axis is perpendicular to the first axis, the second axis or both the first and second axes. In some particular embodiments, the third axis is perpendicular to both the first and second axes. In some embodiments, at least two of said blades are of substantially different sizes in at least one dimension (e.g. length, width or both). In some specific embodiments, said two blades of different sizes form part of the same blade assembly. In other specific embodiments, said two blades of different sizes form parts of different blade assemblies. In some embodiments, at least one of the first, second, third and, when present, fourth blades is a comb-shaped blade. In some embodiments, at least one of the first, second, third and, when present, fourth blades is a substantially flat blade. In some embodiments, the retractor further comprise a means for locking said first blade assembly and second blade assembly in a position apart from each other along said second axis. In some embodiments, the method further comprises removing at least a part of said means for moving the first and second blade assemblies toward and away from each other along the second axis. In some embodiments, the incision is made in the lumbar region of the back near the spine. In some embodiments, the method further comprises placing one or more pedicle screws in the spine of the body. In other embodiments, the method further comprises adjusting the first and second blade assemblies to closed positions and removing the retractor from the incision, thereby returning the incision to substantially the same shape and size as prior to retractor insertion. In still further embodiments, at least one blade assembly is removable. In specific embodiments, both blade assemblies are removable.

In some embodiments, the invention provides a kit for performing an operation, comprising: (a) a retractor comprising: (i) a first blade assembly comprising a first blade rotatable about a first axis, a second blade rotatable about said first axis and an adjuster in mechanical communication with the first and second blades and adapted to rotate the first and second blades relative to each other about said first axis; (ii) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (iii) a means for moving said first blade assembly relative to said second blade assembly along a third axis that is not parallel to said first and second axes; and (b) at least one member of the group consisting of instructions for using the retractor to perform a surgical operation, scalpels, suture needles, pedicle screws, suture material, spinal implant material, spinal fusion rods, biocompatible adhesive and closure staples. In some embodiments, the second blade assembly of the retractor comprises a third blade, a fourth blade and an adjuster in mechanical communication with the third and fourth blades and adapted to rotate the third and fourth blades relative to each other about said second axis. In some embodiments, the first and second axes are substantially coplanar with one another. In specific embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor further comprises a means for locking said first and second blade assemblies in at least one predetermined position along said second axis. In some embodiments, two of said blades are of substantially different sizes in at least one dimension. In particular embodiments, two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some specific embodiments, both blade assemblies are removable.

In some embodiments, the invention provides a retractor comprising: (a) a first arm having a distal end and a proximal end; (b) a second arm having a distal end and a proximal end; (c) a first blade assembly, attached near the distal end of the first arm and comprising a first blade, a second blade and an adjuster in mechanical communication with the first and second blades and adapted to rotate the first and second blades relative to each other about a first axis; (d) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (e) an actuator adapted to move at least the distal ends of said first and second arms relative to each other along a third axis that is not parallel to the first and second axes. In some embodiments of the retractor, the second blade assembly comprises a third blade, a fourth blade and an adjuster in mechanical communication with the third and fourth blades and adapted to rotate the third and fourth blades relative to each other about said second axis. In some embodiments, the first and second axes are substantially coplanar with one another. In some embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor further comprises a means for locking said first and second blade assemblies in at least one predetermined position along said second axis. In some embodiments, at least two of said blades are of substantially different sizes in at least one dimension (e.g. length, width or both). In some embodiments, two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some embodiments, both blade assemblies are removable. In some embodiments, the actuator comprises a stabilizer which maintains at least a portion of each of the first and second arms in an attitude substantially parallel to each other when the first and second arms are moved toward and away from each other. In some embodiments, the stabilizing member comprises a first crosspiece having first and second ends, a second crosspiece having third and fourth ends, the first and second crosspieces being connected to each other by a pivot, the first end of the first crosspiece being connected to the first arm by a pivot, the second end of the first crosspiece being slidably connected to the second arm, the third end of the second crosspiece being connected to the second arm by a pivot and the fourth end of the second crosspiece being slidably connected to the first arm. In some specific embodiments, the first end of the first crosspiece is connected to the first arm at a position distal to the slidable connection of the fourth end of the second crosspiece to the first arm. In some more specific embodiments, the third end of the second crosspiece is connected to the second arm at a position distal to the slidable connection of the second end of the first crosspiece to the second arm. In some embodiments, the retractor further comprises a lock adapted to reversibly hold said first and second arms apart from each other along the second axis. In some specific embodiments, the lock is a ratchet lock comprising a ratchet blade and a ratchet release. In some more specific embodiments, the ratchet lock holds the first arm and the second arm apart from each other along the second axis. In some embodiments, the actuator comprises a first handle connected to the proximal end of the first arm and a second handle connected to the proximal end of the second handle, wherein the first handle and the second handle are adapted to move the distal ends of the first and second arms toward and away from each other along the second axis. In some specific embodiments, the first and second handles are connected by a pivot. In some additional embodiments, the actuator further comprises a biasing member adapted to bias the actuator toward a preselected condition. In some specific embodiments, the biasing member is a biasing spring. In some embodiments, the biasing spring biases the distal ends of the first and second arms toward each other.

In some embodiments, the invention provides a method (e.g. a surgical method for surgery on the spine, e.g. the lumbar region of the spine) comprising the steps of: (a) providing a retractor comprising: (i) a first arm having a distal end and a proximal end; (ii) a second arm having a distal end and a proximal end; (iii) a first blade assembly, attached near the distal end of the first arm and comprising a first blade, a second blade and an adjuster in mechanical communication with the first and second blades and adapted to rotate the first and second blades relative to each other about a first axis; (iv) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (v) an actuator adapted to move at least the distal ends of said first and second arms relative to each other along a third axis that is not parallel to the first and second axes; (b) ensuring that the first and second blades of the first blade assembly are substantially parallel to each other to form a first closed blade assembly; (c) ensuring that the third blade, and when present the fourth blade, of the second blade assembly are substantially parallel to the first and second blades of the first blade assembly; (d) making an incision in a tissue of a body; (e) inserting said first blade assembly and said second blade assembly within the incision; (f) actuating the retractor such that said first blade assembly and second blade assembly are moved apart from one another along the second axis and the incision is stretched along the length of the incision to create an opening longer than the incision; and (g) adjusting the first and second blades of the first blade assembly along said first axis to an open position, and, when said fourth blade of said second blade assembly is present, adjusting the third and fourth blades of the second blade assembly substantially along said second axis to an open position, thereby stretching the incision along the first axis and creating an aperture in the tissue that is longer and wider than the incision. In some embodiments, the method optionally comprises adjusting the third and fourth blades of the second blade assembly to an open position. In some embodiments, the actuator comprises a means for locking the first and second arms in a position apart from each other along the second axis, wherein the method further comprises locking said first and second arms in a position apart from each other along the second axis. In some embodiments, the actuator further comprises a set of removable handles, the method optionally further comprising removing said set of removable handles from the first and second arms. In other embodiments, the incision is made in the lumbar region of the back near the spine. In further embodiments, the method further comprises placing one or more pedicle screws in the spine of the body. In some embodiments the method further comprises closing the first and second blade assemblies and removing the retractor from the incision, thereby returning the incision to substantially the same shape and size as prior to retractor insertion.

In some embodiments, the invention provides a kit (e.g. a surgical kit, especially a spinal surgery kit, and most particularly a spinal surgery kit for surgery on the lumbar region of the spine. In some embodiments, the kit comprises: (a) a retractor comprising: (i) a first arm having a distal end and a proximal end; (ii) a second arm having a distal end and a proximal end; (iii) a first blade assembly, attached near the distal end of the first arm and comprising a first blade, a second blade and an adjuster in mechanical communication with the first and second blades and adapted to rotate the first and second blades relative to each other about a first axis; (iv) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (v) an actuator adapted to move at least the distal ends of said first and second arms relative to each other along a third axis that is not parallel to the first and second axes; and (b) at least one member of the group consisting of instructions for using the retractor to perform a surgical operation, scalpels, suture needles, pedicle screws, suture material, spinal implant material, spinal fusion rods, biocompatible adhesive and closure staples. In some embodiments, the second blade assembly comprises a third blade, a fourth blade and an adjuster in mechanical communication with the third and fourth blades and adapted to rotate the third and fourth blades relative to each other about said second axis. In some embodiments, the first and second axes are substantially coplanar with one another. In some embodiments, the first and second axes are coplanar with one another. In some embodiments, the third axis is substantially perpendicular to the first axis, the second axis or both the first and second axes. In some specific embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor further comprises a means for locking said first and second blade assemblies in at least one predetermined position along said second axis. In some embodiments, two of said blades are of substantially different sizes in at least one dimension. In some embodiments, at least two blades of different sizes form part of the same blade assembly. In some specific embodiments, two blades of different sizes form parts of different blade assemblies. In some other embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some specific embodiments, both blade assemblies are removable. In some embodiments, the actuator comprises a stabilizer which maintains at least a portion of each of the first and second arms in an attitude substantially parallel to each other when the first and second arms are moved toward and away from each other. In some specific embodiments, the stabilizing member comprises a first crosspiece having first and second ends, a second crosspiece having third and fourth ends, the first and second crosspieces being connected to each other by a pivot, the first end of the first crosspiece being connected to the first arm by a pivot, the second end of the first crosspiece being slidably connected to the second arm, the third end of the second crosspiece being connected to the second arm by a pivot and the fourth end of the second crosspiece being slidably connected to the first arm. In some embodiments, the first end of the first crosspiece is connected to the first arm at a position distal to the slidable connection of the fourth end of the second crosspiece to the first arm. In some embodiments, the third end of the second crosspiece is connected to the second arm at a position distal to the slidable connection of the second end of the first crosspiece to the second arm. In some embodiments, the retractor further comprises a lock adapted to reversibly hold said first and second arms apart from each other along the second axis. In some specific embodiments, the lock is a ratchet lock comprising a ratchet blade and a ratchet release. In some more specific embodiments, the ratchet lock holds the first arm and the second arm apart from each other along the second axis. In some embodiments, the actuator comprises a first handle connected to the proximal end of the first arm and a second handle connected to the proximal end of the second handle, wherein the first handle and the second handle are adapted to move the distal ends of the first and second arms toward and away from each other along the second axis. In some embodiments, the first and second handles are connected by a pivot. In some embodiments, the actuator further comprises a biasing member adapted to bias the actuator toward a preselected condition. In some embodiments, the biasing member is a biasing spring. in some specific embodiments, the biasing spring biases the distal ends of the first and second arms toward each other.

In some embodiments, the invention provides a retractor comprising: (a) a first arm having a distal end and a proximal end; (b) a second arm having a distal end and a proximal end, at least said distal end of said first arm and said distal end of said second arm being movable toward and away from each other; (c) a first blade assembly attached near the distal end of the first arm, which comprises a first blade, a second blade and a means for moving said first and second blades relative to each other about a first axis to adopt at least an opened position and a closed position; (d) a second blade assembly attached near the distal end of the second arm, which comprises a third blade, a fourth blade and a means for moving said third and fourth blades relative to each other about a second axis different from said first axis; and (e) a means for moving at least said distal end of said first arm and said distal end of said second arm relative to one another along a third axis that is not parallel to said first and second axes. In some embodiments, the first and second axes are substantially coplanar with one another. In some specific embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some specific embodiments, the third axis is perpendicular to both the first and second axes. In some embodiments, the retractor further comprises a means for locking said first and second blade assemblies in at least one predetermined position along said second axis. In some embodiments, two of said blades are of substantially different sizes in at least one dimension. In some embodiments, two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some embodiments, both blade assemblies are removable. In some embodiments, the means for moving at least said distal end of said first arm and said distal end of said second arm relative to one another along the second axis comprises a means for maintaining at least a portion of each of the first and second arms in an attitude substantially parallel to each other when the first and second arms are moved toward and away from each other. In some embodiments, the retractor further comprises a means for locking the first and second arms in at least one preselected position. In some embodiments, the means for moving at least said distal end of said first arm and said distal end of said second arm toward along said third axis comprises a removable means for moving said first arm and said second arm relative to each other along the second axis. In some embodiments, the removable means for moving said first arm and said second arm toward and away from each other further comprises a means for biasing the arms toward or away from each other.

The invention further provides a method (e.g. a method of surgery, such as spinal surgery, and in particular spinal surgery in the lumbar region of the back) comprising the steps of: (a) providing a retractor comprising: (i) a first arm having a distal end and a proximal end; (ii) a second arm having a distal end and a proximal end, at least said distal end of said second arm and said distal end of said second arm being movable toward and away from each other; (iii) a first blade assembly attached near the distal end of the first arm, which comprises a first blade, a second blade and a means for moving said first and second blades relative to each other along a first axis to adopt at least an opened position and a closed position; (iv) a second blade assembly attached near the distal end of the second arm, which comprises a third blade, a fourth blade and a means for moving said third and fourth blades relative to each other substantially along the first axis to adopt at least an opened position and a closed position; and (v) a means for moving at least said distal end of said first arm and said distal end of said second arm relative to one another along a second axis; (b) ensuring that the first and second blades of the first blade assembly are substantially parallel to each other; (c) ensuring that the third and fourth blades of the second blade assembly are substantially parallel to each other and to the first and second blades of the first blade assembly; (d) making an incision in a tissue of a body; (e) inserting said first blade assembly and said second blade assembly within the incision; (f) actuating the retractor such that said first blade assembly and second blade assembly are moved apart from one another along the second axis and the incision is stretched along the length of the incision to create an opening longer than the incision; and (g) adjusting the first and second blades of the first blade assembly along said first axis to an open position, and, when said fourth blade of said second blade assembly is present, adjusting the third and fourth blades of the second blade assembly substantially along said second axis to an open position, thereby stretching the incision along the first axis and creating an aperture in the tissue that is longer and wider than the incision. In some embodiments, the actuator comprises a means for locking the first and second arms in a position apart from each other along the second axis, the method optionally further comprising locking said first and second arms in a position apart from each other. In some embodiments, the actuator further comprises a set of removable handles, optionally further comprising removing said set of removable handles from the first and second arms. In some embodiments, the incision is made in the lumbar region of the back near the spine. In some embodiments, the method further comprises placing one or more pedicle screws in the spine of the body. In some embodiments, the method further comprises closing the first and second blade assemblies and removing the retractor from the incision, thereby returning the incision to substantially the same shape and size as prior to retractor insertion.

The invention further provides a kit comprising: (a) a retractor comprising: (i) a first arm having a distal end and a proximal end; (ii) a second arm having a distal end and a proximal end, at least said distal end of said first arm and said distal end of said second arm being movable toward and away from each other; (iii) a first blade assembly attached near the distal end of the first arm, which comprises a first blade, a second blade and a means for moving said first and second blades relative to each other along a first axis to adopt at least an opened position and a closed position; (iv) a second blade assembly attached near the distal end of the second arm, which comprises a third blade, a fourth blade and a means for moving said third and fourth blades relative to each other substantially along the first axis to adopt at least an opened position and a closed position; and (v) a means for moving at least said distal end of said first arm and said distal end of said second arm relative to one another along a second axis; and (b) at least one member of the group consisting of instructions for using the retractor to perform a surgical operation, scalpels, suture needles, pedicle screws, suture material, spinal implant material, spinal fusion rods, biocompatible adhesive and closure staples. In some embodiments, the first and second axes are substantially coplanar with one another. In some embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor of the kit further comprises a means for locking said first and second blade assemblies in at least one predetermined position along said second axis. In some embodiments, at least two of said blades are of substantially different sizes in at least one dimension. In some embodiments, at least two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some embodiments, both blade assemblies are removable. In some embodiments, the means for moving at least said distal end of said first arm and said distal end of said second arm relative to one another along the second axis comprises a means for maintaining at least a portion of each of the first and second arms in an attitude substantially parallel to each other when the first and second arms are moved toward and away from each other. In some embodiments, the retractor of the kit further comprises a means for locking the first and second arms in at least one preselected position. In some embodiments, the means for moving at least said distal end of said first arm and said distal end of said second arm toward along said third axis comprises a removable means for moving said first arm and said second arm relative to each other along the second axis. In some embodiments, the removable means for moving said first arm and said second arm toward and away from each other further comprises a means for biasing the arms toward or away from each other.

The present invention further provides, in some embodiments, a retractor blade assembly, comprising: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope, (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions. In some embodiments of the blade assembly the third angle is opposite in sign and congruent with the first angle and the fourth angle is opposite in sign and congruent with the second angle. In some embodiments of the blade assembly at least the first angle has a magnitude with respect to the axis of less than about 75.degree. In some embodiments of the blade assembly, each angle has a magnitude with respect to the axis of less than about 75.degree. In some embodiments of the blade assembly each angle has a magnitude with respect to the axis of about 20.degree. to about 70.degree. In some embodiments of the blade assembly, each channel has a first end and a second end and the nut and plunger are threaded so that the rod moves from the first end of the channels to the second end within 1 to 10 full rotations of the nut. In some embodiments of the blade assembly, the rod moves from the first end to the second end of the channels within 2 to 8 full rotations of the nut. In some embodiments of the blade assembly the rod moves from the first end to the second end of the channels within 3 to 6 full rotations of the nut. In some embodiments of the blade assembly, the rod moves from the first end to the second end of the channels within 4 to 6 full rotations of the nut. In some embodiments of the blade assembly, at least one blade is comb shaped. In some embodiments of the blade assembly, both blades are comb shaped. In some embodiments of the blade assembly, at least one blade is fan shaped. In some embodiments of the blade assembly, both blades are comb shaped. In some embodiments of the blade assembly, the holder is adapted to be removably affixed to an arm of a retractor. In some embodiments of the blade assembly, the holder is irreversibly affixed to an arm of a retractor.

Thus, the invention provides a retractor as described herein, wherein at least one blade assembly is a retractor blade assembly, comprising: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope, (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions. In some embodiments, the third angle is opposite in sign and congruent with the first angle and the fourth angle is opposite in sign and congruent with the second angle. In some embodiments, at least the first angle has a magnitude with respect to the axis of less than about 75.degree. In some embodiments, each angle has a magnitude with respect to the axis of less than about 75.degree. In some embodiments, each angle has a magnitude with respect to the axis of about 20.degree. to about 70.degree. In some embodiments, each channel has a first end and a second end and the nut and plunger are threaded so that the rod moves from the first end of the channels to the second end within 1 to 10 full rotations of the nut. In some embodiments, the rod moves from the first end to the second end of the channels within 2 to 8 full rotations of the nut. In some embodiments, the rod moves from the first end to the second end of the channels within 3 to 6 full rotations of the nut. In some embodiments, the rod moves from the first end to the second end of the channels within 4 to 6 full rotations of the nut. In some embodiments, at least one blade is comb shaped. In some embodiments, both blades are comb shaped. In some embodiments, at least one blade is fan shaped. In some embodiments, both blades are comb shaped. In some embodiments, the holder is adapted to be removably affixed to an arm of a retractor. In some embodiments the holder is irreversibly affixed to an arm of a retractor.

In some embodiments, the invention provides a kit comprising a retractor as described herein, wherein at least one blade assembly comprises: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope; (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions.

In some embodiments, the invention provides a method as described herein using a retractor as described herein, wherein at least one blade assembly is a retractor blade assembly, comprising: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope; (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions.

The invention will now be further described with reference to the appended drawings. In FIG. 1 there is shown a perspective view of a retractor 10 according to the present invention. The retractor 10 comprises a first arm 12, having a distal end 14 to which is attached a first blade assembly 16, comprising a first blade 18, a second blade 20 and an adjuster 22; a second arm 32, having a distal end 34, to which is attached a second blade assembly 36 comprising a third blade 38, a fourth blade 40 and an adjuster 42. The retractor further comprises a first handle 24 having a distal end 28 and a proximal end 26 and a second handle 44 comprising a distal end 48 and a proximal end 46. The two handles 24 and 44 are joined to one another by a pivot 50 and are spanned by a biasing spring 52. The retractor 10 further comprises a ratchet lock 54, which has serrations 56 that are adapted to engage an engagement member 58, which together with the ratchet lock 54 serves to hold the retractor in a particular position. In FIG. 1, the retractor 10 is shown in the "closed" position, meaning that the two blade assemblies 16 and 36 are relatively close to one another, as are the two arms 12 and 32 and the distal ends 28 and 48 of the handles 24 and 44, respectively. Depression of the proximal ends 26 and 46 of handles 24 and 44, respectively, in the directions of the arrows a and b results in the blade assemblies 16 and 36 moving apart along the directional arrows c and d, thus causing retractor 10 to assume the configuration depicted in FIG. 2. Note that the directional arrows c and d define a geometric line passing through and joining axis f, which passes vertically through first adjuster 22, and axis g, which passes vertically through second adjuster 42. Hereinafter axis f may be referred to alternatively as a first axis, axis g may be referred to alternatively as a second axis and the axis defined by directional arrows c and d may alternatively be referred to as a third axis. The importance of these axes will become evident upon consideration of the remaining figures.

Figure 2:
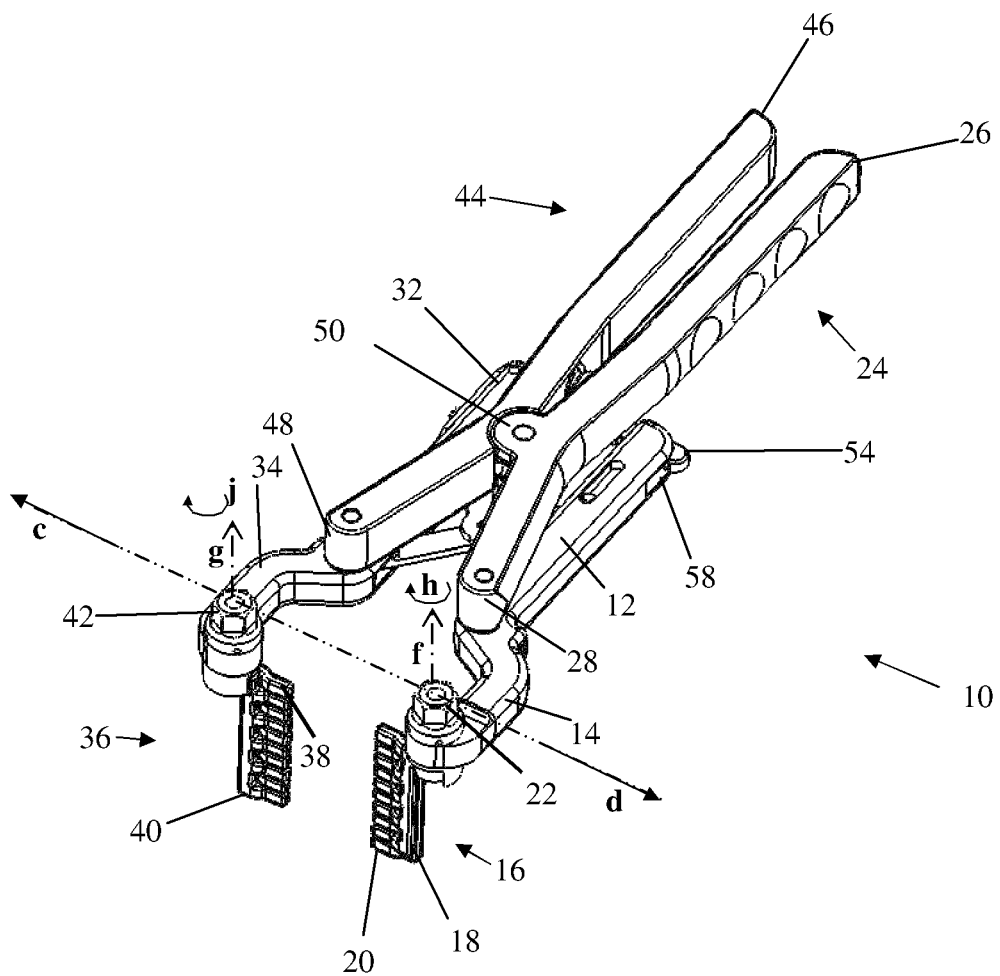
FIG. 2 provides a perspective view of a retractor of the invention, this time with the blades open in one direction along directional arrows c and d. Opening the retractor in this direction stretches the incision along its length.

As can be seen in FIG. 2, the retractor 10 is in an "open" position, meaning that the first blade assembly 16 is relatively separated from the second blade assembly 36 along the third axis defined by directional arrows c and d. Thus, as the blade assembly 16 moves along line d and blade assembly 36 moves along line c they exert force in the direction of lines d and c, respectively. Insertion of the blade assemblies 16 and 36 into an incision (not shown) in a closed position (as in FIG. 1) and opening the blade assemblies 16 and 36 to an open position (as in FIG. 2) results in a stretching of the incision along the same axis defined by directional lines c and d.

It is noted that in the embodiment depicted in FIGS. 1 and 2, the actuator comprises a pair of arms 12 and 32 and a pair of handles 24 and 44. The person skilled in the art will recognize that other embodiments of an actuator may be used. For example, scissor-like actuators are known in the clamp and retractor arts. In some such embodiments, the actuator comprises a pair of handles such as those depicted in FIG. 1 having attached at the distal ends of the handles 28 and 48 a pair of blade assemblies 16 and 36 according to the invention. Moreover, while the handles 24 and 44 are depicted as being roughly parallel and joined together at a pivot point 50, it is also within the skill in the art to use a pair of crossed (e.g. scissor-like) handles joined by a pivot. These and other embodiments of actuators are known in the art and contemplated as being within the scope of some aspects of the invention. It is also to be understood that when the actuator is a scissor-like embodiment, the motion of blade assemblies 16 and 36 traverse an arc rather than a straight line upon opening of the retractor. Nevertheless, the spatial relationship of the two blade assemblies 16 and 36 can be conceptualized as changing along a line described by arrows c and d, which for the purpose of brevity is referred to herein as an axis, and in particular the third axis (axes f and g being the first and second axes).

Figure 3:
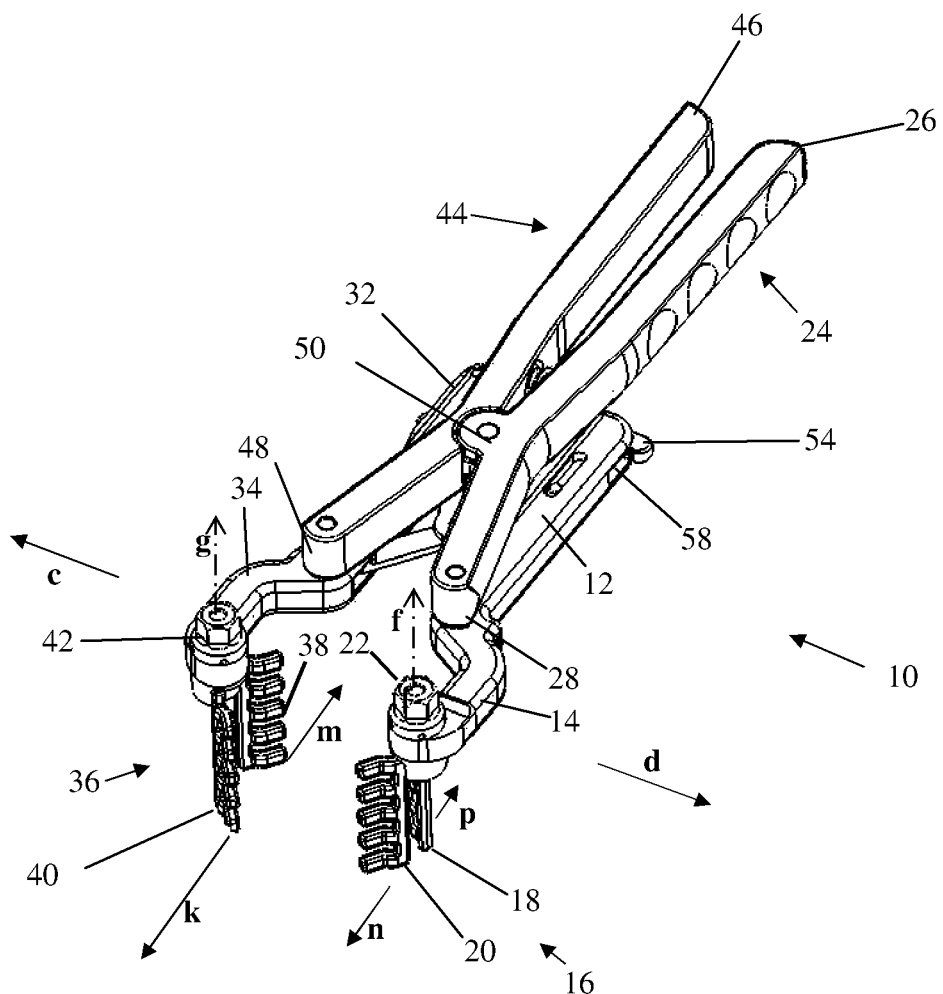
FIG. 3 provides a perspective view of a retractor of the invention, now with the two blade assemblies open in separate directions from the first direction of opening. Opening the retractor blade assemblies stretches the incision open in a second direction that is different from, and essentially not parallel to, the first direction.

Turning adjuster 22 about axis f in the direction of adjustment arrow h, and adjuster 42 about axis g in the direction of adjustment arrow j, results in opening of the blade assemblies 16 and 36, respectively, as depicted in FIG. 3. As shown in FIG. 3, opening of the blade assembly 16 causes the blade 20 to exert force in the direction of direction arrow n, while blade 18 exerts force in the direction of direction arrow p. Likewise, opening of blade assembly 36 causes blade 40 to exert force in the direction of arrow k, while blade 38 exerts force in the direction of arrow m. Thus, after insertion of the closed blade assemblies 16 and 36 of a closed retractor 10 in an incision, opening the retractor 10 and then opening the blade assemblies 16 and 36, the retractor 10 creates and maintains an aperture in the incised tissue that is both longer (i.e. dimensionally larger in the direction of the incision) and wider (i.e. dimensionally larger in a direction perpendicular or oblique to the direction of the incision) than the incision. It is to be understood that, while this description is especially apt where the incision is a straight line incision of about 0.1 to about 3 inches in length, it can apply to any shape of incision (e.g. an arc, a sinusoid, etc.) of any length. In particular embodiments of the invention, the contemplated size of the incision is about 0.5 to 2 inches in length and the blade assemblies 16 and 36 are appropriately sized so that when the retractor 10 is closed the blade assemblies 16 and 36 fit lengthwise within the incision without requiring substantial stretching of the incised tissue prior to opening of the retractor 10. Thus, in some embodiments, the blades 18, 20, 38 and 40 are sized to snugly fit within the incision when the blade assemblies are closed and the retractor is in a closed position.

Figure 4:
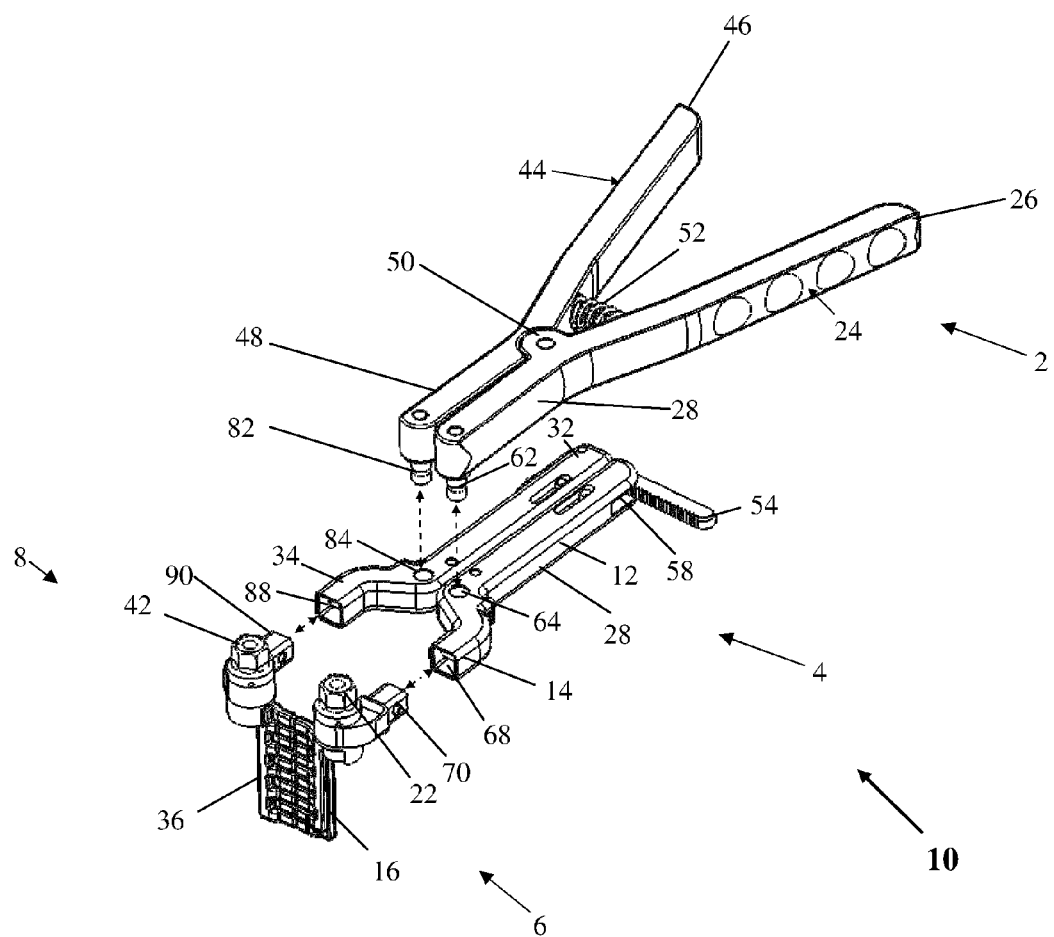
FIGS. 4, 5 and 6 provide exploded perspective views of a retractor of the invention, the handles being separated from the arm assembly and the blade assemblies being separated from the arm assembly.

FIG. 4 shows the device 10 with handle assembly 2, comprising inter alia the handles 24 and 44, separated from arm assembly 4, comprising inter alia arms 12 and 32. As can be seen in FIG. 4, the distal end 28 of handle 24 has a connecting pin 62 that fits within a connecting hole 64 on the first arm 12, while the distal end 48 of handle 44 has a connecting pin 82 that fits within a connecting hole 84 in the arm 32. In the depicted embodiment, the blade assembly 16 is removable from the distal end 14 of arm 12 and the blade assembly 36 is removable from the distal end 34 of arm 32. As depicted, the blade assembly 16 can be connected to the arm 12 by inserting the projection 70 on the proximal end of holder 6 within orifice 68 in the distal end 14 of arm 12. Likewise blade assembly 36 can be connected to arm 32 by inserting the projection 90 on the proximal end of holder 8 within the orifice 88 in the distal end 34 of arm 32.

Figure 5:
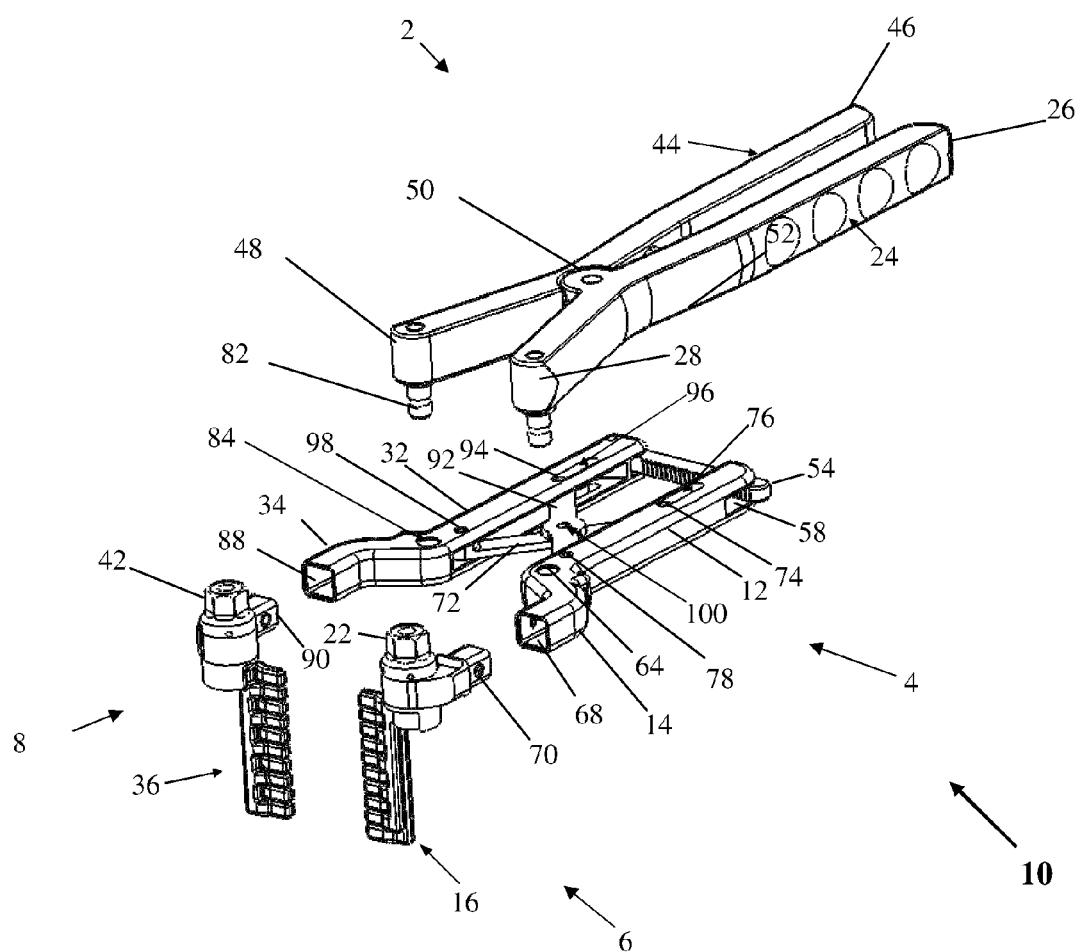
Figure 12:
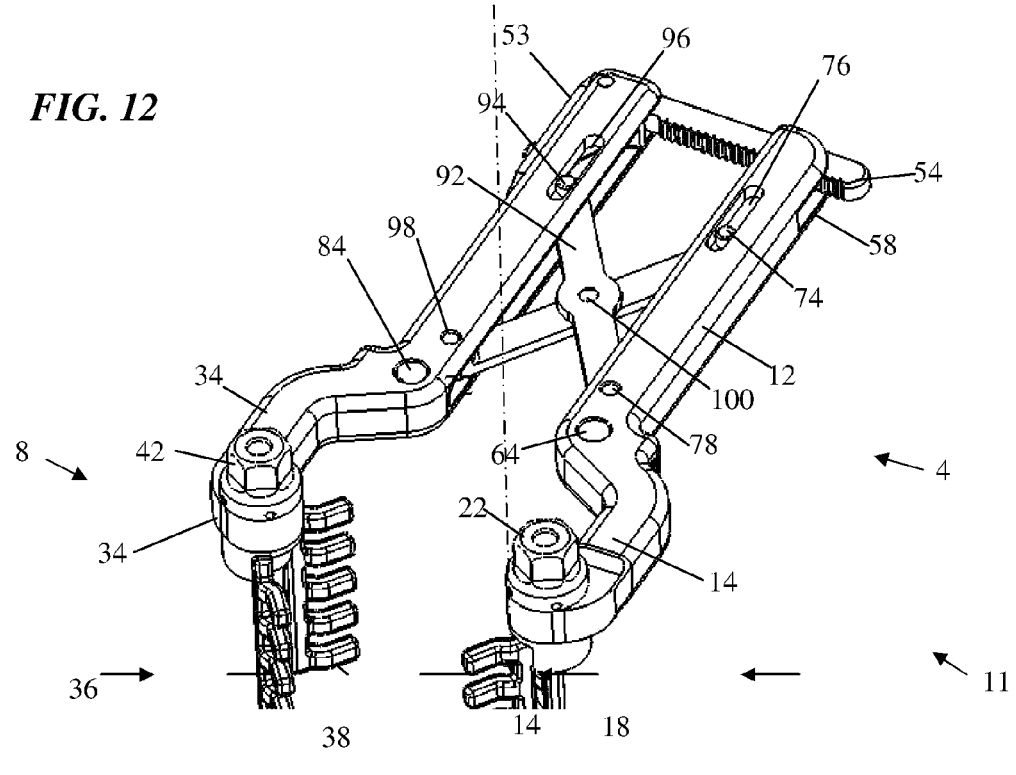
FIG. 12 provides a perspective view of an arm assembly of the invention.

FIG. 5 depicts the arms 12 and 32 of the arm assembly 4 in an open position. In this position it can be seen that arms 12 and 32 are joined one to another by a pair of cross members 72 and 92, which are joined together by a cross member pivot 100. The cross member 72 is connected to arm 32 via a pivot 98 and to arm 12 via a rod 74, which is moveable along the length of slot 76. Likewise the cross member 92 is connected to arm 12 via a pivot 78, and to arm 32 via a rod 94, which is moveable along the length of slot 96. One skilled in the art will recognize that the handle assembly 2 may be removed from the arm assembly 4 by removing the pins 62 and 82 from their respective holes 64 and 84, resulting in the device 11 depicted in FIG. 12. This may occur at any time, e.g. prior to or during sterilization of the retractor 10 or during a surgical procedure once the retractor 10 has been opened. Removal of the handle assembly 2 during surgery may afford a member of the surgical team greater freedom of motion, an improved field of view or both.

As can be seen in FIGS. 4 and 5, the blade assemblies 16 and 36 can be removed from the arm assembly 4. One may find it convenient to remove the blade assemblies 16 and 36 in order to expedite sterilization of the blade assemblies 16 and 36 and/or in order to exchange one or both blade assemblies 16 and 36 for other blade assemblies (e.g. different size blades, different configuration of blades, etc.) as discussed in more detail herein.

Figure 6:
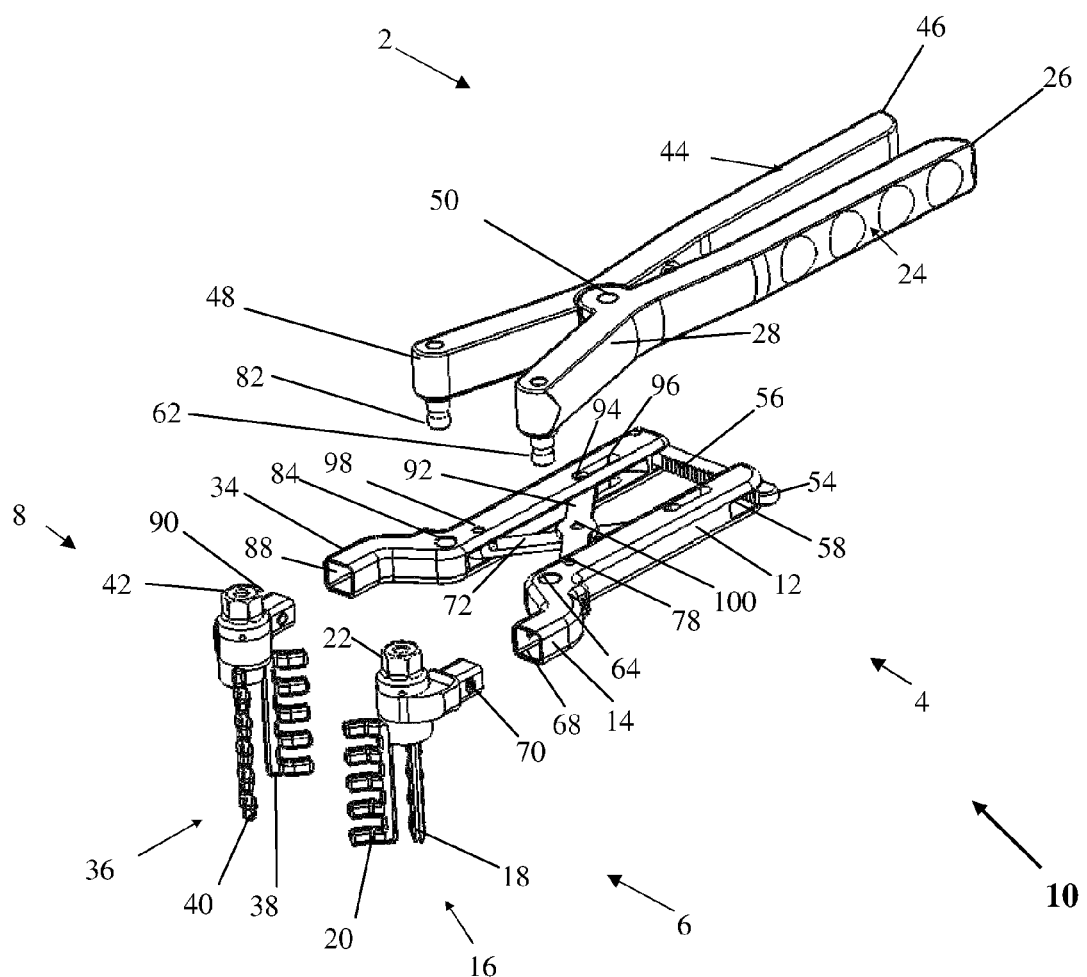
Figure 7:
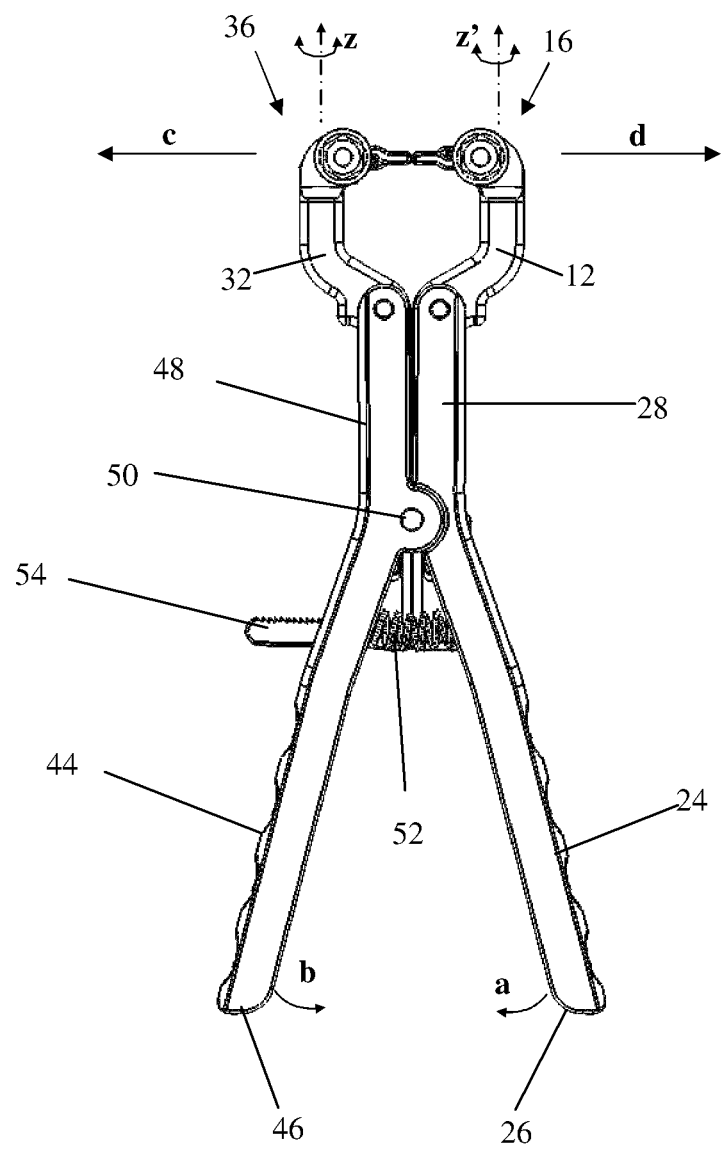
FIGS. 7, 8 and 9 provide top views of the retractor of the invention.
Figure 8:
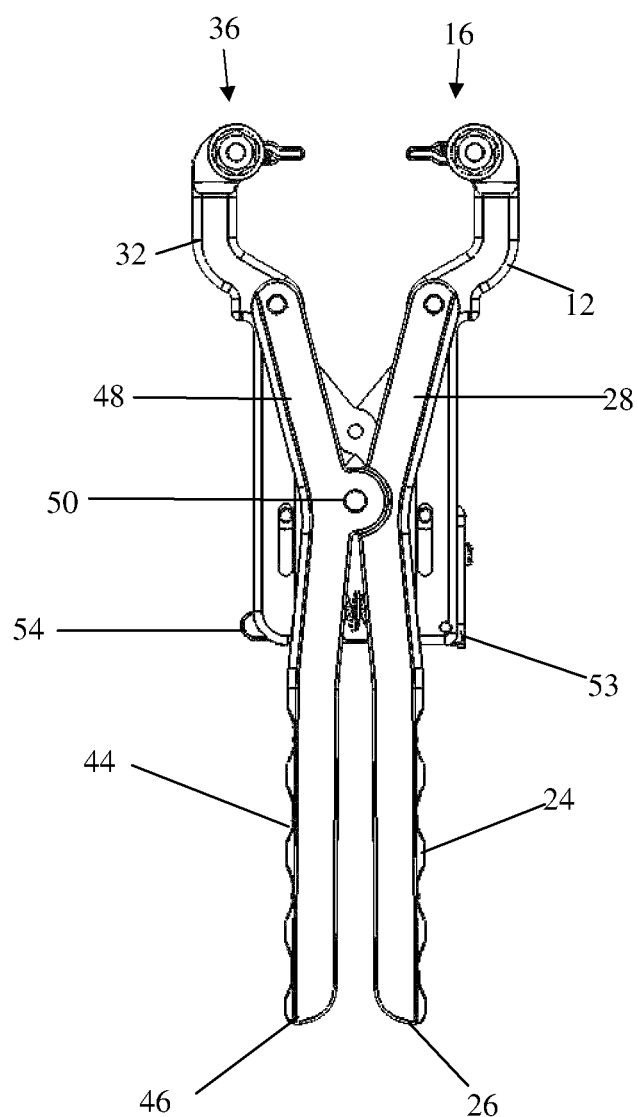
Figure 9:
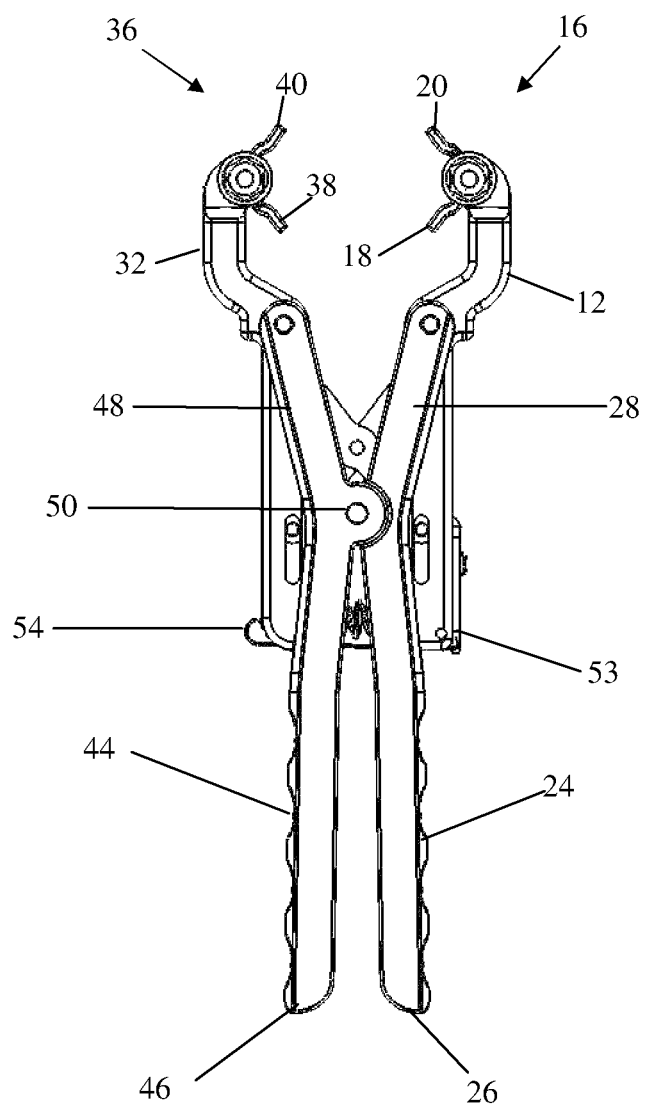
Figure 10:
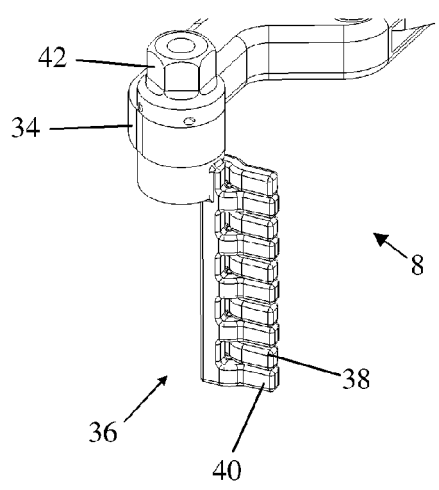
FIGS. 10 and 11 provide close-up views of a blade assembly of the invention.
Figure 11:
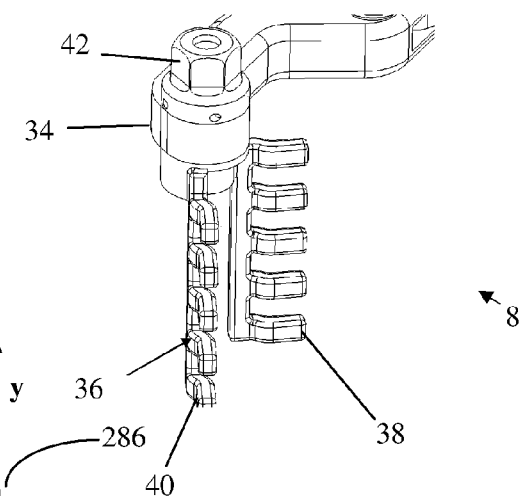

FIG. 6 is an exploded view of the retractor 10 with the blade assemblies 16 and 36 in an open position. FIG. 7 is a view of retractor 10 from above in a closed position. In this view it can be clearly seen that the biasing spring 52 tends to bias the handles 12 and 32 apart. Also shown in this view are axes z and z'. In some embodiments, the blade assemblies 16 and 36 are adapted to rotate about the axes z, z'. In some embodiments, these added degrees of freedom permit the blade assemblies 16, 36 to be rotated outward so that they are farther apart at the lower parts of the blades than at the top. This allows the retractor 10 to create an even larger aperture without having to open the retractor 10 any farther. FIG. 8 shows a top view of the retractor 10 in an open position. As shown in FIG. 8 the ratchet 54 locks into position to hold the retractor 10 in an open position. FIG. 9 shows the retractor 10 from above with the blade assemblies 16 and 36 in open positions. FIGS. 10 and 11 are expanded views of blade assembly 36 in closed (FIG. 10) and open (FIG. 11) positions.

Figure 30:
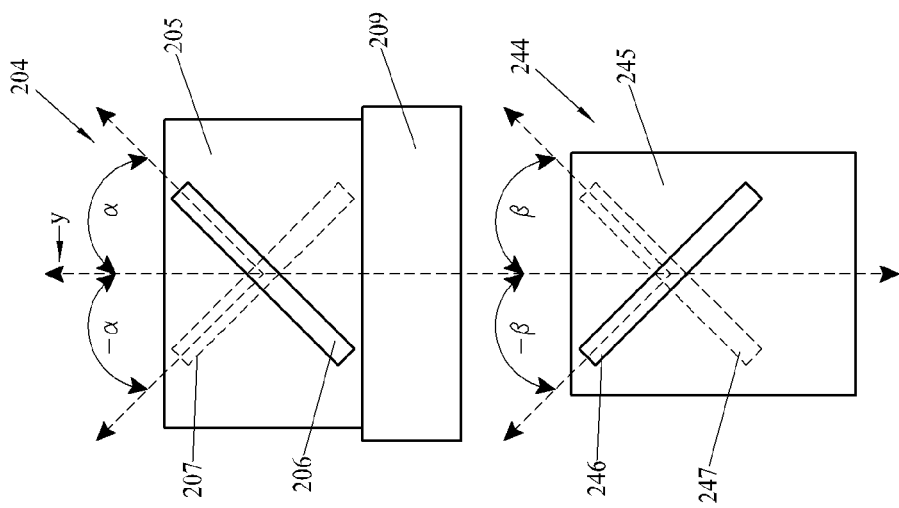
FIGS. 29-30 show side views of barrels of blade assemblies according to the invention.
Figure 29:
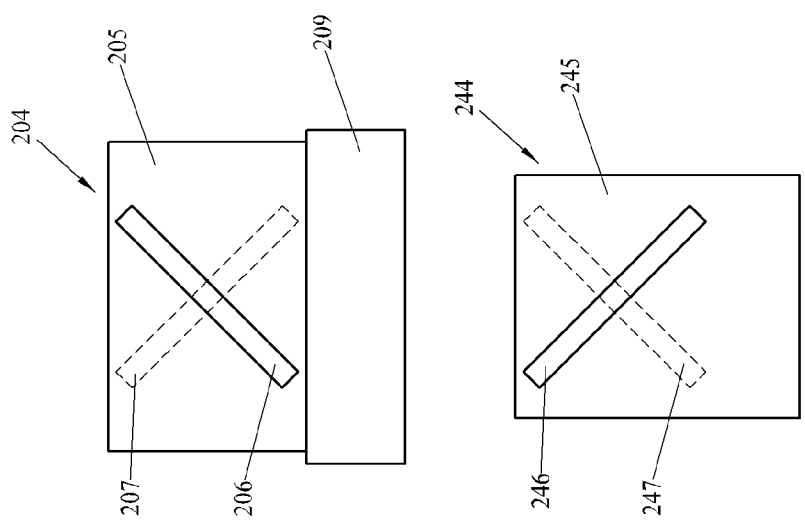

FIGS. 13-19 depict the assembly of an embodiment of a blade assembly 36, which comprises blades 40 and 38. Starting with FIG. 13, left opening blade subassembly 242 comprises blade 40, which is connected to inner barrel 244. The blade 40 comprises a plurality of teeth 254 connected to a bridge 252, which in turn is connected to the inner barrel 244 such that rotating the inner barrel 244 about axis y to the left (clockwise) results in the teeth 254 also turning to the left (clockwise). The inner barrel 244 has a slot 246 cut into the upper portion 245 of the inner barrel 244. Specifically, the upper portion 245 of the inner barrel 244 is that portion of the inner barrel 244 above the highest point at which the bridge 252 connects to the inner barrel 244. Not shown in this view is a corresponding slot on the other side of barrel 244, which is depicted in FIGS. 29 and 30 as slot 247, as discussed in more detail herein. The inner barrel 244 also has a lumen 248 through the inner barrel 244 and an engagement groove 250 circumscribing the inner barrel 244 above the slot 246.

Figure 31:
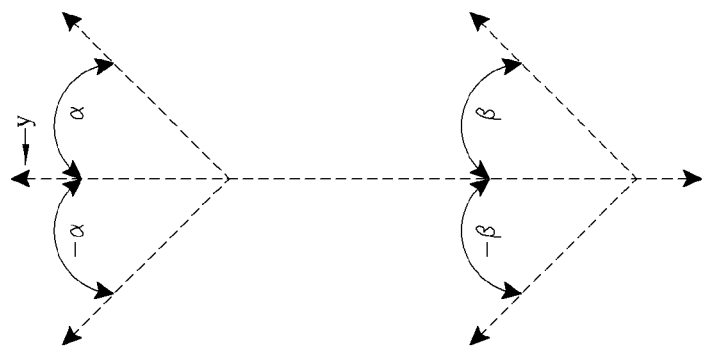

The right opening blade subassembly 202 comprises blade 38 comprising teeth 214 connected to a bridge 212, which in turn is attached to the outer barrel 204. The outer barrel 204 also possesses a lip 209, which is a ledge about the lower portion of the barrel 204. The bridge 212 is connected to the lip 209 such that rotation of the outer barrel 204 to the right (counterclockwise) about axis y results in the blade 38 also turning to the right (counterclockwise) about the axis y. The outer barrel 204 has a lumen 208 as well as a pair of slots 206, 207 cut into upper portion 205 of the barrel 204. For the sake of clarity, the upper portion 205 of the outer barrel 204 is that portion of the outer barrel 204 above the lip 209. The relationship of the slots 206, 207, 246 and 247 are depicted in FIGS. 29-31.

In FIG. 29 there is depicted a side view of barrel outer barrel 204 and inner barrel 244. For purposes of clarity, the barrels 244 and 204 are depicted without the additional components of the blade sub-assemblies attached, such as the blades. As can be seen in FIG. 29, slot 206 penetrates the upper portion 205 of outer barrel 204. Slot 207, shown in dotted lines, also penetrates the upper portion 205 of the outer barrel 204, albeit on the opposite side of the outer barrel 204. The outer barrel 204 also has a lip 209, as mentioned above, which is below the upper portion 205 of the outer barrel 204. Slot 246 penetrates the upper portion 245 of inner barrel 244. Slot 247, shown in dotted lines, also penetrates the upper portion 245 of the inner barrel 244, albeit on the opposite side of the inner barrel 244. As shown in FIG. 30, the inner barrel 244 and the outer barrel 204 have a common axis y, which passes vertically through the lumens (not shown) of the barrels 244 and 204. Axis y thus forms a C2 symmetry axis for slots 206 and 207, as well as for slots 246 and 247. More specifically, slot 206 forms an angle .alpha. with respect to the y axis, whereas the slot 207 forms an angle –.alpha. with respect to the axis y. Viewed from the vantage offered in FIG. 29, these angles .alpha. and –.alpha. have equal magnitude but opposite slope with respect to the axis y. In a like manner, the slot 246 forms an angle .beta., with respect to the axis y and the slot 247 forms an angle –.beta. with respect to the axis y. Thus slots 206 and 207 possess C2 symmetry about the axis y, as rotation of inner barrel 244 about the axis y results in slots 246 and 247 equivalently changing places, as these slots possess congruent angles with respect to the y axis and are located 180.degree. about the axis y from one another. Similarly, the slots 246 and 247 possess C2 symmetry about the axis y, as rotation of the slots 246 and 247 about the y results in slots 206 and 207 changing places, as these slots are essentially identical with respect to the y axis. Note that .alpha. and –.beta. have similar orientation as do –.alpha. and .beta. This accounts for the opposite rotation of the barrels 204, 244. Note also that in this embodiment angles .alpha., .beta., –.alpha. and –.beta. are essentially congruent, although in some embodiments of the invention it may be desirable for .alpha. and –.alpha. to differ in magnitude from .beta. and –.beta. One of skill in the art would recognize that this latter arrangement would cause barrels 204 and 244 to rotate at different rates in opposite directions. Additionally, in the depicted embodiment it is presumed that the slots 206 and 207 are of equal length and start and end at essentially the same height as each other. However, it will be understood that the length of the slots 206 and 207 may be affected inter alia by the method used to form such features in the barrel 204 (e.g. machining, molding, etc.) and the assignment of C2 symmetry to the slot pair 206, 207 is intended as an illustrative convenience. More specifically, it is intended that breaking the strict mathematical C2 symmetry of the slots 206, 207 will not affect the operation of the invention. Likewise breaking the strict mathematical C2 symmetry of the slots 246, 247 will not affect operation of the invention. Thus, lengthening or shortening one of slots 206 or 207, moving one of the slots 206 or 207 up or down the barrel (along the axis y) or both changing the length and the position of one of the slots 206, 207 will not defeat the purpose of the invention. Similarly, lengthening or shortening one of slots 246 or 247, moving one of the slots 246 or 247 up or down the barrel (along the axis y) or both changing the length and the position of one of the slots 246, 247 will not defeat the purpose of the invention. Thus, for the slot pair 206, 207 to satisfy the C2 symmetry requirement for the purposes of the present invention, it is sufficient that a portion of the slots 206, 207 satisfy the C2 symmetry requirement. Likewise, it is sufficient for a portion of the slot pair 246, 247 to satisfy the C2 symmetry requirement in order for the slot pair 246, 247 to satisfy the C2 symmetry requirement for the purposes of the present invention. However, in the currently preferred embodiment, the slot pair 206, 207 possess strict C2 symmetry, as does the slot pair 246, 247, within reasonable tolerances (e.g. about +/−2%). It is also noted that, while the slots 206, 207, 246 and 247 are depicted as having constant slope with respect to the axis y, it is possible and well within the skill in the art for the slots to have serpentine or other curved slopes with respect to the axis y so long as the C2 symmetry requirement is satisfied through at least a portion of the slot pairs 206, 207 and 246, 247. (FIG. 31 shows the angles .alpha., –.alpha., .beta. and –.beta. independent of the barrels in order to provide easier visualization of their relationships to one another.)

Figure 13:
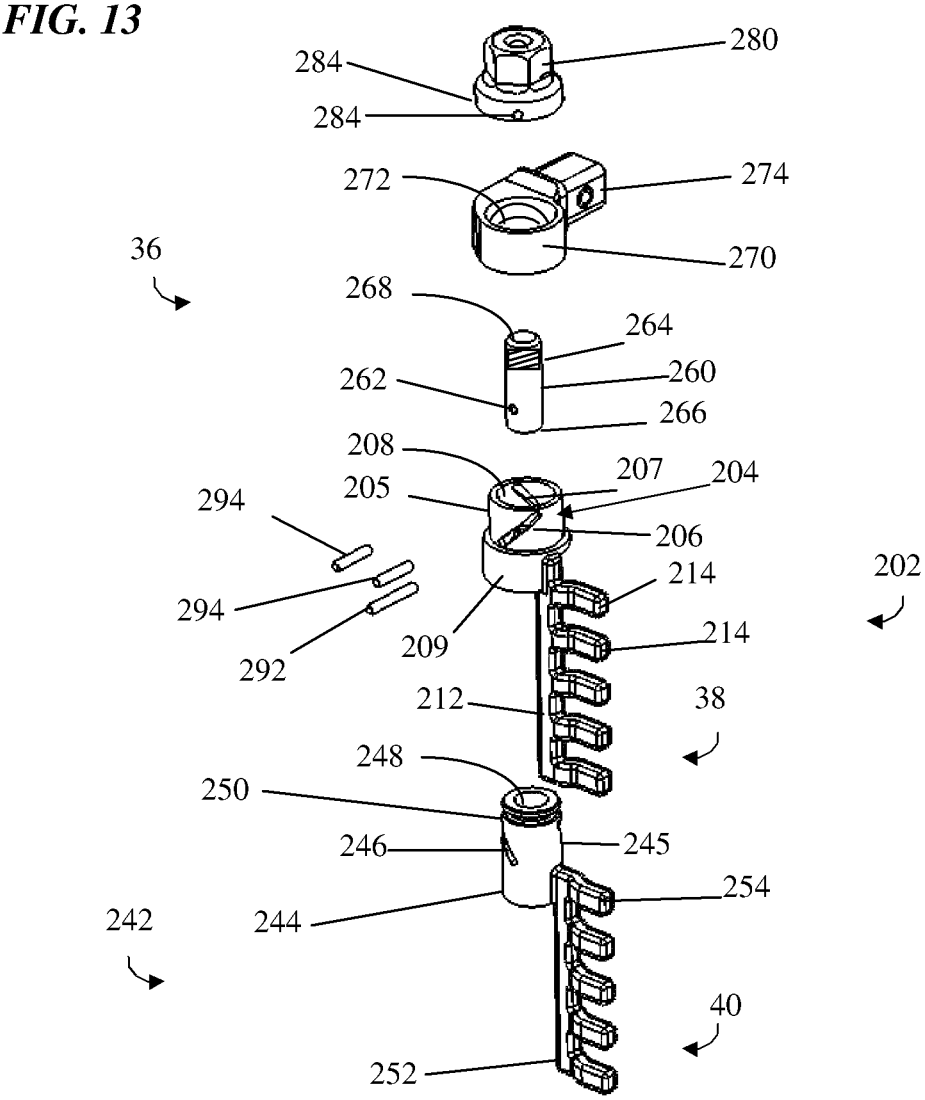
FIGS. 13-19 provide exploded views of a blade assembly of the invention, from which the assembly and operation of the blade assembly can be discerned.

FIG. 13 further depicts threaded plunger 260 having a bottom 266 and a top 268. The plunger 260 has a set of screw threads 265 near the top 268 and a hole 262 at a right angle to and passing through the y axis. Also depicted is a holder 270 comprising a lumen 272 and a projection 274. Additionally there is depicted an adjustment nut (or adjuster) 280 having internal threads 286 and two engagement holes 284. Also depicted are a connector pin 292 and two engagement pins 294.

Figure 14:
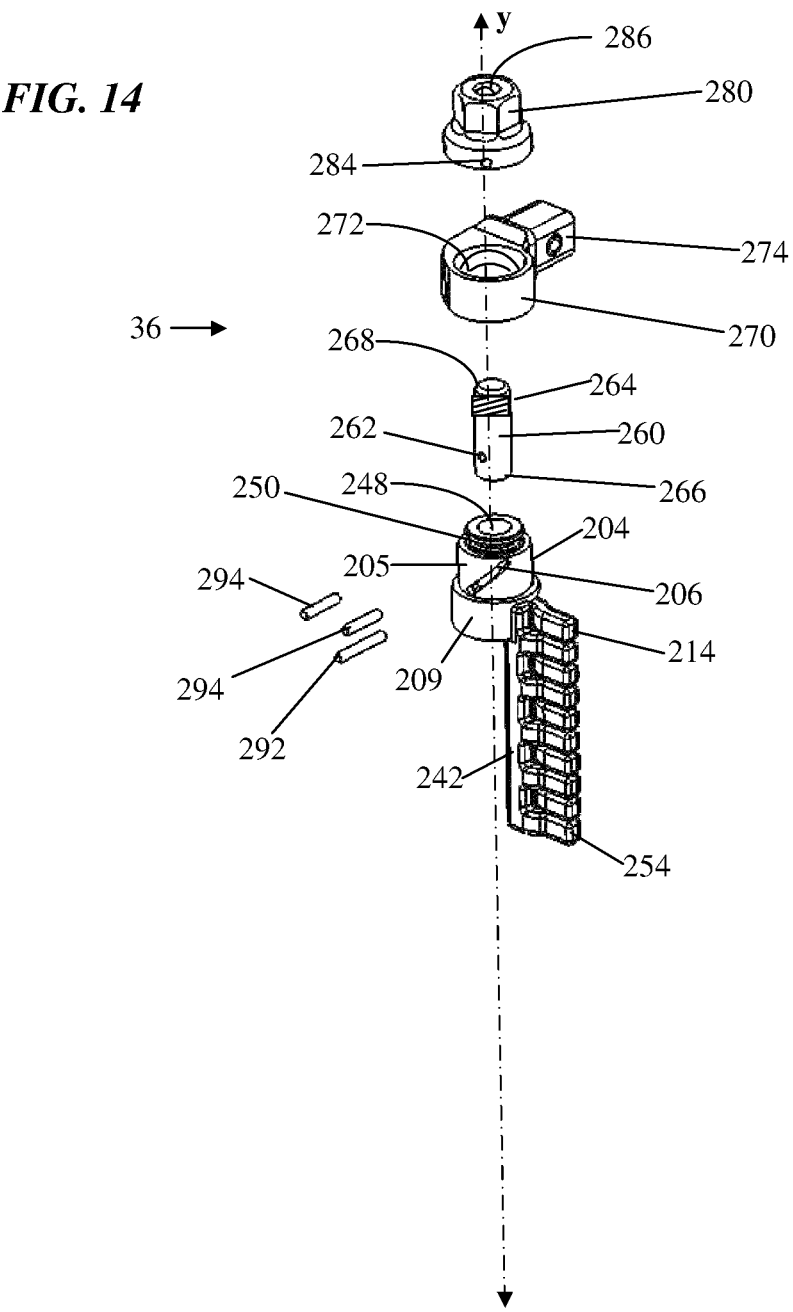
Figure 15:
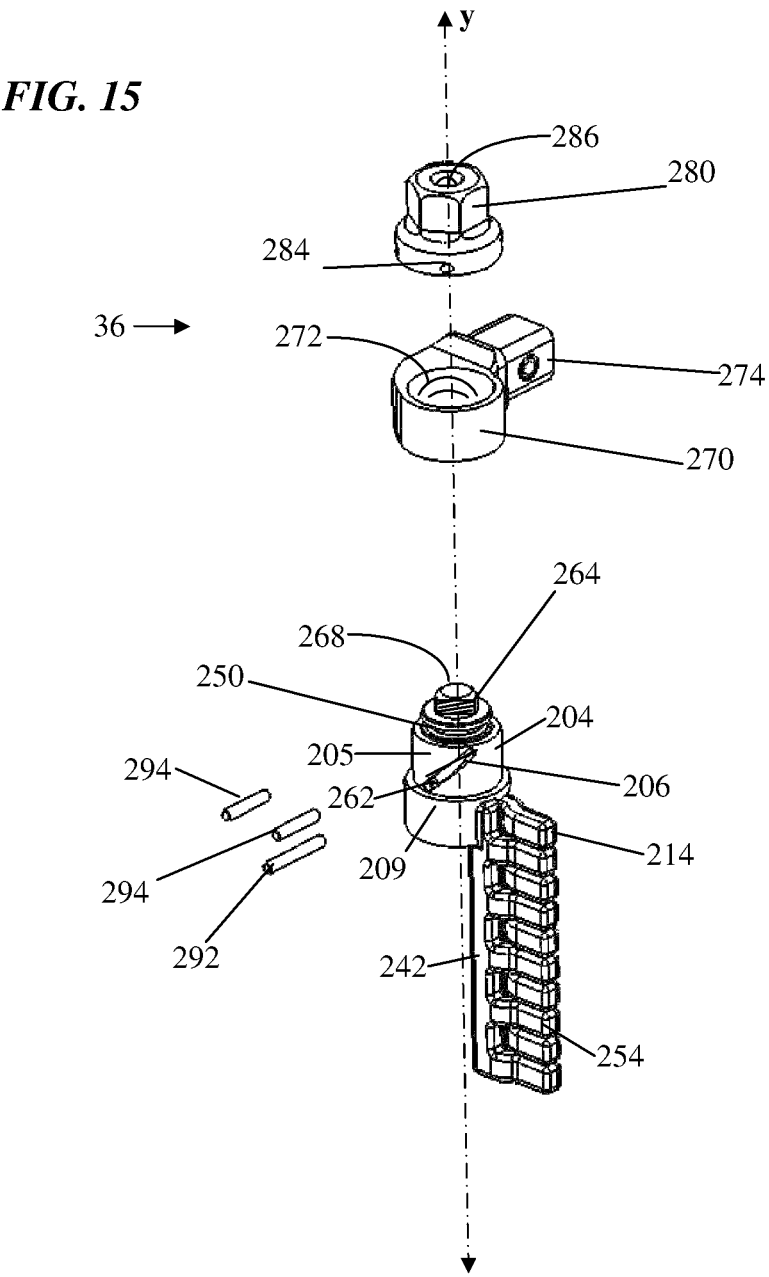
Figure 16:
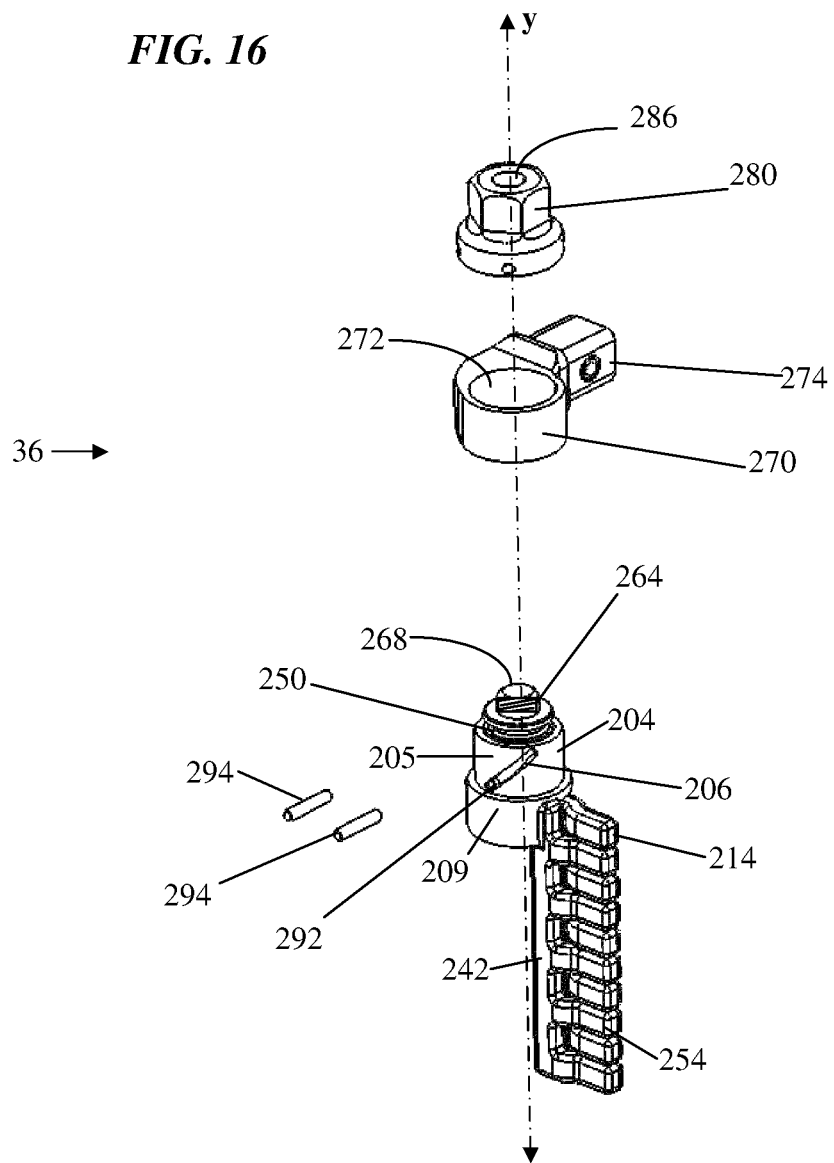
Figure 17:
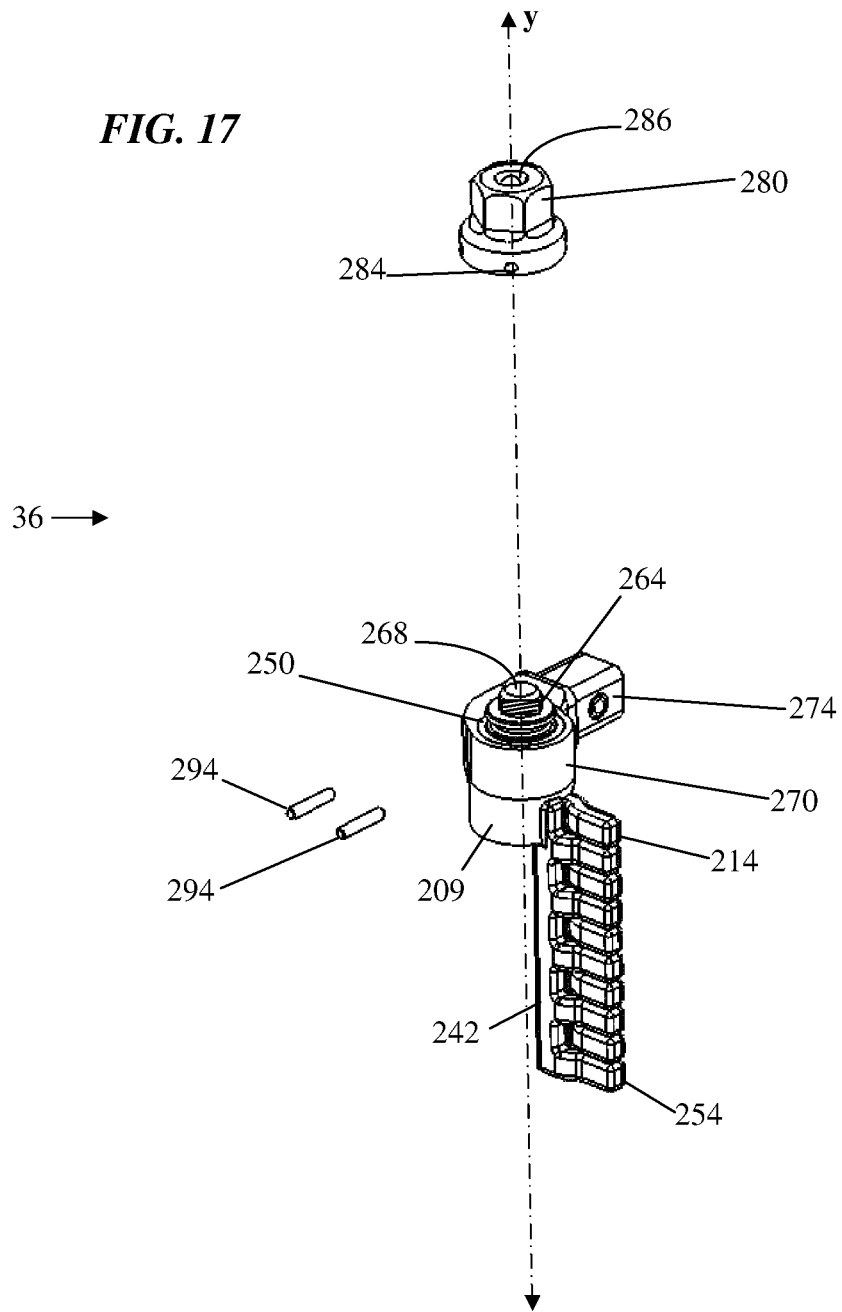
Figure 18:
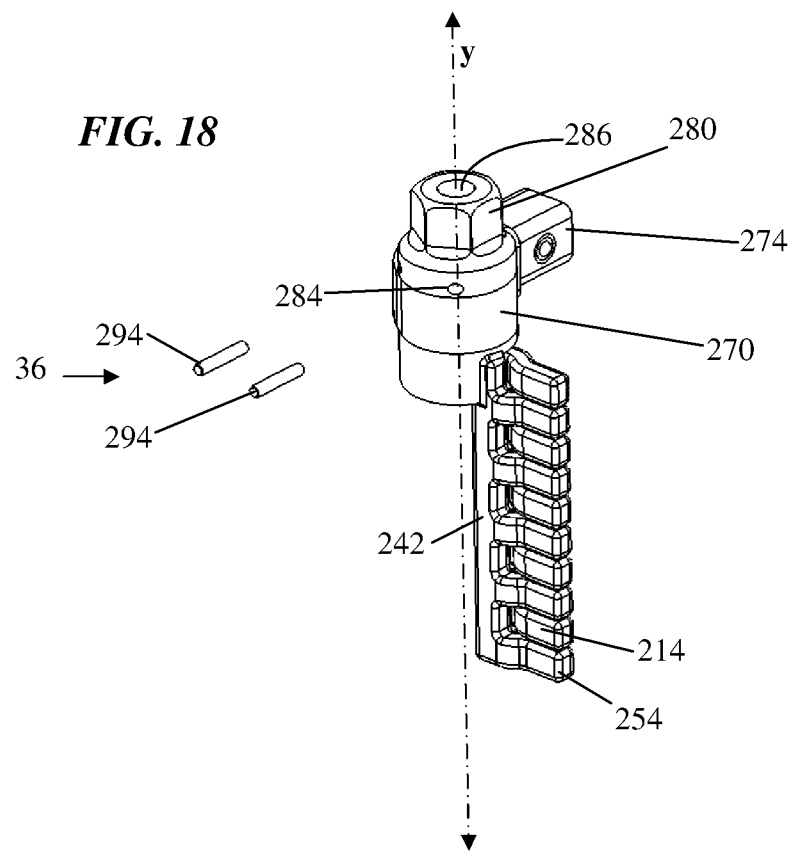
Figure 19:
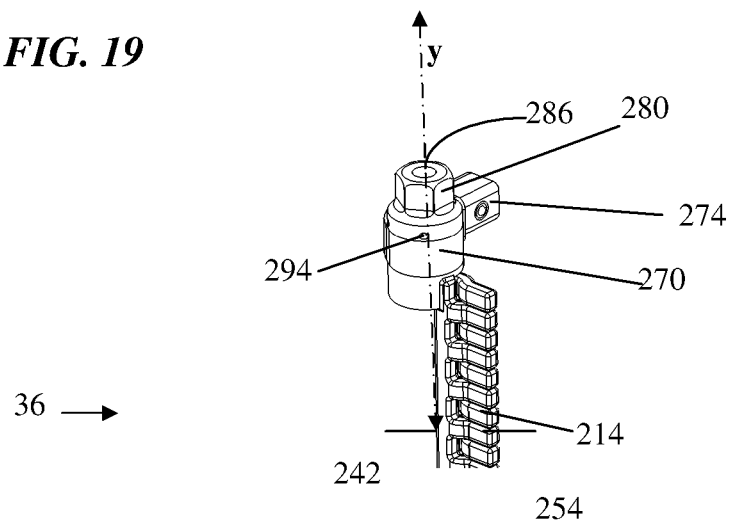
Figure 27:
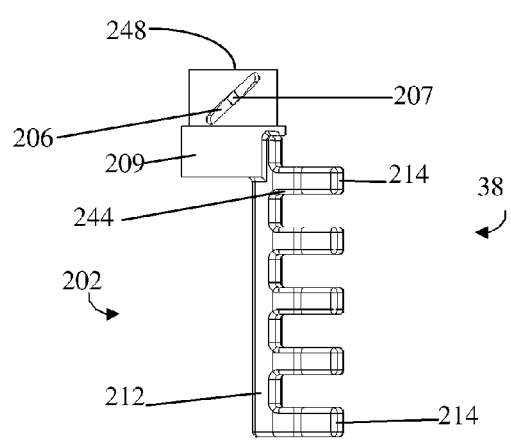
FIGS. 26-28 show side views of a second blade of a blade assembly.
Figure 28:
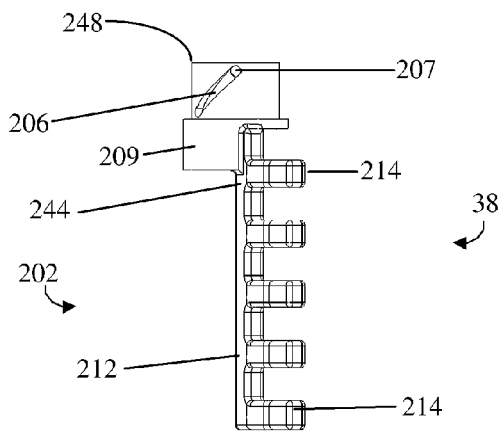

As seen in FIG. 14, the left turning barrel 244 fits within the lumen 208 of the right turning barrel 204. The plunger 260 then fits within the lumen 248 of the left turning barrel 244, as depicted in FIG. 15. In this configuration, the left turning slot 246 crosses the right turning slot 206 forming a passage 261 through which, as depicted in FIG. 16, the connector pin 292 fits. As depicted in FIG. 16, the blades 38 and 40 are in a closed position with the connector pin 292 at the bottom of the slots 24. In this configuration, it is seen that the two blades 38, 40 interlace to form a substantially planar blade pair, thus rendering the blade pair especially suitable for insertion within a small incision. One skilled in the art will recognize that moving the blades 38 and 40 apart will cause the barrels 244 and 204 to rotate in opposite directions, thereby causing connector pin 292 to rise along slots 246 and 206, thereby causing the plunger 260 to rise along the y axis. Conversely, pulling the plunger 260 up along the y axis would cause the connector pin 292 to rise along the slots 246 and 206, thereby causing the barrels 244 and 204 to rotate in opposite directions, thus causing the blades 40 and 38 to move apart. Conversely, starting with the connector pin 292 at the top of slots 246 and 206, pressing the plunger 260 down will cause the connector pin 292 to move down the slots 246 and 206, thereby causing the barrels 244 and 204 to rotate in opposite directions, thereby causing the blades 38 and 40 to rotate toward one another. As can be seen in FIG. 17, the assembly of barrel 244, barrel 204 and plunger 260 fits through the lumen 272 of the holder 270 so that the threads 264 toward the end 268 of the plunger 260 are visible above the lumen 272 of the holder 270 and the lip 209 of the outer barrel 204 abuts the holder 270. As can be seen in FIG. 18, the adjustment nut (adjuster) 280 fits over the end 268 of the plunger 260 and is held in place by pushing the engagement pins 294 through the engagement holes 284. One of skill in the art will appreciate that the engagement pins 294 thus engage the engagement groove 250 on the barrel 244, thereby permitting the adjustment nut 280 to freely turn about the y axis, but preventing the adjustment nut 280 from moving up or down along the y axis. The inner threads 286 of the adjustment nut 280 thus engage the outer threads 264 of the plunger 260. Turning the adjustment nut 280 about the y axis in one direction causes the plunger 260 to move upward along the y axis, while turning the adjustment nut 280 in the opposite direction causes the plunger 260 to move downward along the y axis. As explained above, movement of the plunger 260 causes movement of the connector pin 292 up and down the y axis. Movement of the pin 260 in one direction creates force in one direction on the slots in one barrel and in the opposite direction on the slots in the other barrel. Thus, the adjustment nut 280 can be turned to open an close the blade assembly 36. FIG. 19 shows a fully assembled blade assembly 36 in the closed position.

Figure 20:
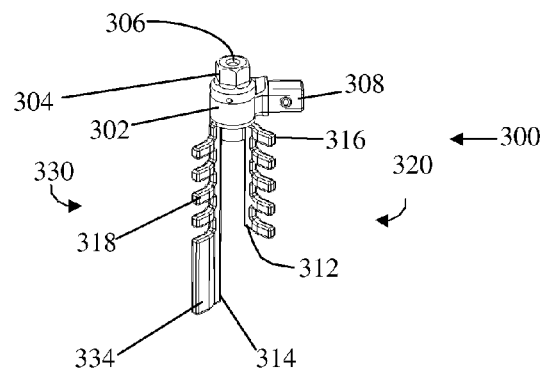
FIGS. 20-22 show various blades that may be employed in blade assemblies of the invention.
Figure 22:
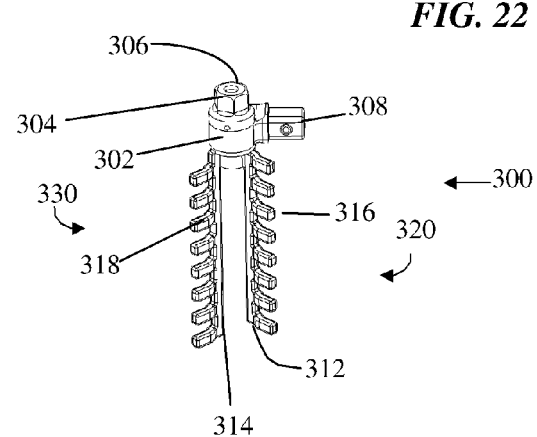

The blades used in the blade assemblies may have a variety of configurations. FIG. 20 shows an alternate embodiment of a blade assembly 300 according to the invention, which comprises a holder 302 connected to a projection 308, which is adapted to reversibly insert into the end of an actuator arm (not shown). The blade assembly 300 further comprises an adjuster 304 and a plunger 306. The adjuster 304 is threaded on the inside, just as the plunger 306 is threaded on its outer surface, so that turning the adjuster causes the plunger 306 to move up and down. The plunger 306 operates through the holder 302 to turn the blades 320, 330 in opposite directions as described in more detail with regard to FIGS. 1-13 above. In particular, the plunger 306 operates to turn inner barrel 322 in the opposite direction to outer barrel 332 essentially as described above. Inner barrel 322 is connected to bridge 312 from which project teeth 316. Together bridge 312 and teeth 316 form the blade 320. Outer barrel 332 is connected to bridge 314 from which project teeth 318 and fan 334. Together bridge 314, teeth 318 and fan 334 form the blade 330.

Figure 21:
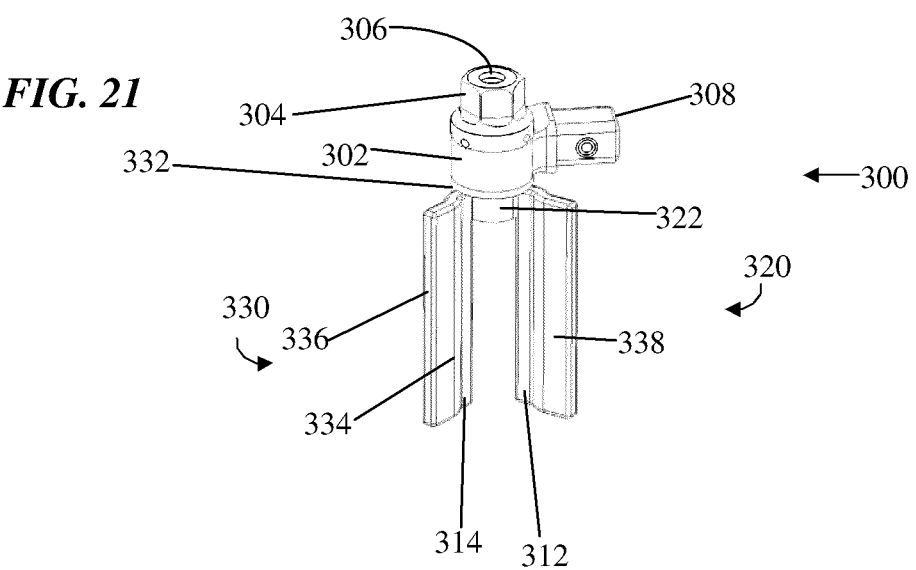
Figure 23:
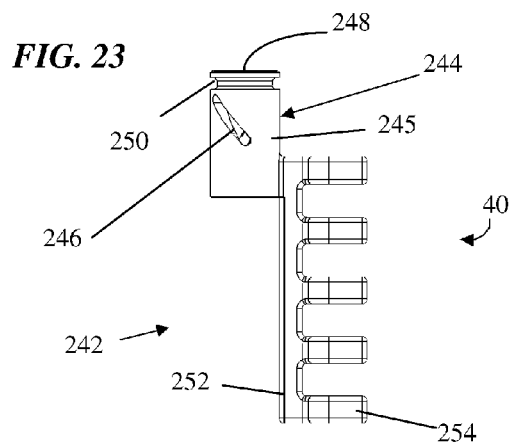
Figure 24:
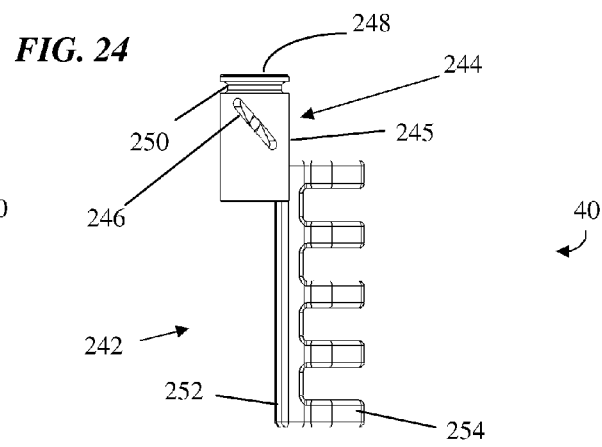
Figure 25:
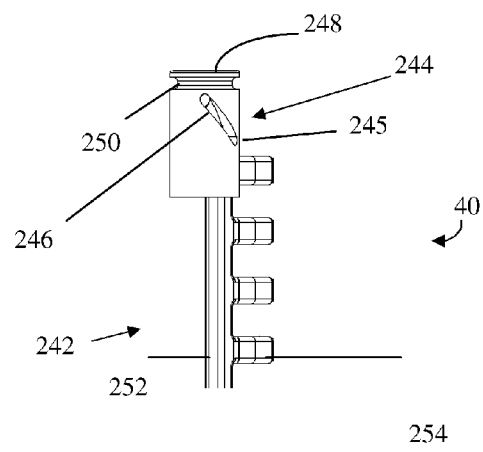
Figure 26:
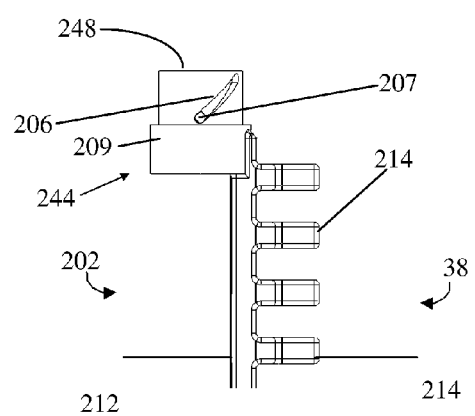

Another embodiment of a blade assembly 300 is shown in FIG. 21, where the blade 320 comprises fan 338; and blade 330 comprises fan 336. As can be seen in FIGS. 22-28, blades 320, 330 can have a variety of lengths of bridges 312, 314, teeth 316, 318, etc. (In these figures, the same numbering is used as in FIGS. 1-13.

In some embodiments, the invention contemplates kits comprising a retractor of the invention. In some embodiments, the kit comprises a single actuator (e.g. a removable handle and arm assembly as described herein and depicted in the figures, a scissor-like assembly, etc.) and a plurality of removable and exchangeable blade assemblies. In some embodiments, the kit comprises at least three blade assemblies having amongst the three blade assemblies at least two distinct blade configurations. In other embodiments, the kit comprises from 3 to 12 blade assemblies having amongst the several blade assemblies from 2 to 12 distinct blade configurations. In some embodiments, the kit comprises at least two pairs of identical or substantially similar blade assemblies. In other embodiments, the kit comprises from 2 to 10, especially about 2 to 5 such pairs of blade assemblies. The blade configurations that are represented in such kits can include comb-like blades, interlocking comb-like blades (as depicted e.g. in FIGS. 1-12), fan-like blades (as depicted in FIG. 21), combinations of toothed and fan-like blades (as depicted in FIG. 20), etc.

It is noted that in some embodiments the threads 286 and 268 can be canted with respect to the y axis to provide mechanical advantage to the operator opening and closing the blade assembly 36. In particular, the threads may be canted so that one full rotation of the nut 280 will result in the connector pin 292 rising from $\frac{1}{10}$ to all the way from its lowest position to its highest position. In some embodiments, the user will be required to perform from about 1 to about 10 full rotations, especially about 2 to about 8 full rotations, and in particular about 2, 3, 4, 5, 6, 7 or 8 full rotations of the nut 280 to cause the connector pin to traverse the length of the slots 206 and 246, thereby moving the blade assembly 36 from its fully open to its fully closed position or vice versa.

A method according to the invention can be visualized by referring to FIGS. 32-35. In FIG. 32, there is depicted a retractor 10 comprising a pair of handles 24, 44 and a pair of blade assemblies 16, 36 as described in more detail herein. An incision I having a length L is made in a suitable tissue, such as the skin overlying or in proximity to the lumbar region of the spine. The blade assemblies 16, 36 are in a closed position and aligned relatively parallel to one another. In FIG. 33, the blade assemblies 16, 36 have been inserted into the incision I. Pressure on handles 24, 44 causes the retractor 10 to open: i.e. blade assemblies 16, 36 move apart from one another in the general directions of directional arrows c, d, respectively. As can be seen in FIG. 34, the incision I is stretched open in the direction of the directional arrows c and d so that it obtains a length L' greater than length L of the incision. Turning the adjusters 22, 24 in the direction of the curved arrows about the axes f and g, respectively results in the opening of the blade assemblies 16, 36, causing the incision I to open as can be seen in FIG. 35. As can be seen in FIG. 35, the aperture A is opened having a length L' and a width W'. The aperture A thus provides an access area of dimensions L'.times.W' for surgical personnel to view the operating field, to pass instruments, sutures, implants and other surgical materials through the aperture. Reversal of the steps outlined in FIGS. 32-35 results in a final incision I having substantially the same length L and essentially no width, just as the original incision I. By way of comparison, in order for a prior art device having a pair of blades to crease such an aperture, the incision I would have to have a length L' and the blades would have to have a width of L'. Thus, the present invention permits the use of a much smaller incision to create the aperture. Thus, the present invention permits less invasive surgical methods, quicker and more comfortable recovery from surgery and potentially cost savings for the medical coverage provider.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A retractor comprising:
   a first arm and a second arm;
   a first blade assembly coupled to the first arm at a first location, the first blade assembly comprising a first blade, a third blade, and a first adjuster coupled to the first blade and the third blade to rotate the first blade and the third blade about a first axis that intersects the first location and is parallel to a longitudinal axis of the first blade, wherein the first blade and the third blade are configured to rotate in opposite rotational directions simultaneously,
   a second blade assembly coupled to the second arm at a second location, the second blade assembly comprising a second blade and a second adjuster coupled to the second blade to rotate the second blade about a second axis that intersects the second location and is parallel to a longitudinal axis of the second blade, wherein the second axis is different from the first axis, wherein the first and second blades can be independently rotated with respect to each other; and
   an actuation mechanism coupled to the first arm and the second arm for separating the first axis and the first blade from the second axis and the second blade along a third axis that extends between the first location and the second location.

2. The retractor of claim 1, wherein the second blade assembly further comprises a fourth blade.

3. The retractor of claim 2, wherein the second adjuster is coupled to the second blade and the fourth blade to rotate the second blade and the fourth blade about the second axis.

4. The retractor of claim 1, wherein the first and second axes are substantially coplanar with one another.

5. The retractor of claim 1, wherein the third axis is substantially perpendicular to at least one of the first axis and the second axis.

6. The retractor of claim 1, wherein at least one of the first blade and the second blade is a substantially flat blade.

7. The retractor of claim 1, further comprising a locking mechanism adapted to lock the first axis and first blade assembly from the second axis and the second blade along a third axis.

8. The retractor of claim 1, wherein at least a part of the retractor is removable after separating the first axis and the first blade from the second axis and the second blade along the third axis.

9. The retractor of claim 1, wherein one or more of the first blade assembly and the second blade assembly are removable.

10. The retractor of claim 3, wherein the second blade and the fourth blade are configured to rotate about the second axis in opposite rotational directions simultaneously.

11. The retractor of claim 1, wherein the longitudinal axis of the first blade is substantially perpendicular to the first arm.

12. The retractor of claim 1, wherein the longitudinal axis of the second blade is substantially perpendicular to the second arm.

13. A retractor comprising:
    a first arm and a second arm;
    a first blade assembly coupled to the first arm at a first location, the first blade assembly comprising a first blade, a third blade, and a first adjuster coupled to the first blade and the third blade to rotate the first blade and the third blade about a first axis that intersects the first location and is parallel to a longitudinal axis of the first blade, wherein the first adjuster is configured to change the distance between an edge of the first blade and an edge of the third blade to open or close the first blade assembly,
    a second blade assembly coupled to the second arm at a second location, the second blade assembly comprising a second blade and a second adjuster coupled to the second blade to rotate the second blade about a second axis that intersects the second location and is parallel to a longitudinal axis of the second blade, wherein the second axis is different from the first axis, wherein the first and second blades can be independently rotated with respect to each other; and
    an actuation mechanism coupled to the first arm and the second arm for separating the first axis and the first blade from the second axis and the second blade.

14. The retractor of claim 13, wherein the second blade assembly further comprises a fourth blade.

15. The retractor of claim 14, wherein the second adjuster is coupled to the second blade and the fourth blade to rotate the second blade and the fourth blade about the second axis.

16. The retractor of claim 15, wherein the second adjuster is configured to change the distance between an edge of the second blade and an edge of the fourth blade to open or close the second blade assembly.

* * * * *